(12) United States Patent
Linschoten

(10) Patent No.: US 9,744,148 B2
(45) Date of Patent: Aug. 29, 2017

(54) KALLIKREIN 7 INHIBITORS

(71) Applicant: SIXERA PHARMA AB, Goteborg (SE)

(72) Inventor: Marcel Linschoten, Vega (SE)

(73) Assignee: SIXERA Pharma AB (SE)

( * ) Notice: Subject to any disclaimer, the term of this patent is extended or adjusted under 35 U.S.C. 154(b) by 0 days.

(21) Appl. No.: 15/113,658

(22) PCT Filed: Jan. 22, 2015

(86) PCT No.: PCT/SE2015/050060
§ 371 (c)(1),
(2) Date: Jul. 22, 2016

(87) PCT Pub. No.: WO2015/112079
PCT Pub. Date: Jul. 30, 2015

(65) Prior Publication Data
US 2017/0000753 A1    Jan. 5, 2017

(30) Foreign Application Priority Data

Jan. 23, 2014    (SE) ...................................... 1430004

(51) Int. Cl.
| | | |
|---|---|---|
| A61K 31/215 | (2006.01) | |
| A61K 31/42 | (2006.01) | |
| A61K 8/49 | (2006.01) | |
| A61K 31/216 | (2006.01) | |
| A61K 8/42 | (2006.01) | |
| A61K 31/422 | (2006.01) | |
| C07D 413/12 | (2006.01) | |
| C07D 261/14 | (2006.01) | |
| C07C 235/16 | (2006.01) | |
| C07C 235/38 | (2006.01) | |

(52) U.S. Cl.
CPC .............. *A61K 31/215* (2013.01); *A61K 8/42* (2013.01); *A61K 8/49* (2013.01); *A61K 31/216* (2013.01); *A61K 31/42* (2013.01); *A61K 31/422* (2013.01); *C07C 235/16* (2013.01); *C07C 235/38* (2013.01); *C07D 261/14* (2013.01); *C07D 413/12* (2013.01); *C07C 2601/08* (2017.05)

(58) Field of Classification Search
CPC .... A61K 31/215; A61K 31/216; A61K 31/42; A61K 8/42; A61K 8/49
USPC .......................................................... 548/240
See application file for complete search history.

(56) References Cited

U.S. PATENT DOCUMENTS

| | | |
|---|---|---|
| 7,872,052 B2 | 1/2011 | Linschoten |
| 8,415,305 B2 | 4/2013 | Krastel et al. |
| 9,006,466 B2 | 4/2015 | Reboud-Ravaux et al. |
| 2004/0044075 A1 | 3/2004 | Staveski et al. |
| 2006/0258651 A1 | 11/2006 | Linschoten |
| 2011/0092437 A1 | 4/2011 | Krastel et al. |
| 2013/0172267 A1 | 7/2013 | Krastel et al. |
| 2014/0148480 A1 | 5/2014 | Reboud-Ravaux et al. |

FOREIGN PATENT DOCUMENTS

| | | |
|---|---|---|
| WO | 03/101941 A2 | 11/2003 |
| WO | 2004/108139 A2 | 12/2004 |
| WO | 2009/000878 A1 | 12/2008 |
| WO | 2009/024527 A1 | 2/2009 |
| WO | 2009/024528 A1 | 2/2009 |
| WO | 2013/010963 A1 | 1/2013 |

OTHER PUBLICATIONS

Torbjorn Egelrud, "Purification and preliminary characterization of stratum corneum chymotryptic enzyme: a proteinase that may be involved in desquamation," J. Invest. Dermatol., 1993, vol. 101, pp. 200-204.

Skytt et al., "Primary substrate specificity of recombinant human stratum corneum chymotryptic enzyme," Biochemical and Biophysical Research Communications, Jun. 15, 1995, vol. 211, No. 2, pp. 586-589.

Yousef et al. "The KLK7 (PRSS6) gene, encoding for the stratum corneum chymotryptic enzyme is a new member of the human kallikrein gene family—genomic characterization, mapping, tissue expression and hormonal regulation," 2000, Gene 254, pp. 119-1281.

Simon et al., "Refined characterization of corneodesmosin proteolysis during terminal differentiation of human epidermis and its relationship to desquamation," The Journal of Biological Chemistry, Issue of Jun. 8, 2001, vol. 276, No. 23, pp. 20292-20299.

Caubet et al., "Degradation of corneodesmosome proteins by two serine proteases of the kallikrein family, SCTE/KLK5/hK5 and SCCE/KLK7/hK7," J. Invest. Dermatol., 2004, vol. 122, pp. 1235-1244.

Brattsand et al., "A proteolytic cascade of kallikreins in the stratum corneum," J. Invest. Dermatol., 2005, vol. 124, pp. 198-203.

Hachem et al., "Sustained serine proteases activity by prolonged increase in pH leads to degradation of lipid processing enzymes and profound alterations of barrier function and stratum corneum integrity," J. Invest. Dermatol., 2005, vol. 125, pp. 510-520.

Nylander-Lundqvist & Egelrud, "Formation of active IL-1/3f om pro-IL-113 catalyzed by stratum corneum chymotryptic enzyme in vitro," Acta Derm. Venereol (Stockh), 1997, vol. 77, pp. 203-206.

Vasilopoulos et al., "Genetic association between an AACC insertion in the 3'UTR of the stratum corneum chymotryptic enzyme gene and atopic dermatitis," J. Invest. Dermatol., 2004, vol. 123, pp. 62-66.

(Continued)

*Primary Examiner* — Kristin Vajda
(74) *Attorney, Agent, or Firm* — Eric L. Sophir; Dentons US LLP

(57) ABSTRACT

The present invention relates to methods for inhibiting the activity of human kallikrein 7 (KLK7) (also known as serine protease stratum corneum chymotryptic enzyme, SCCE). The invention further relates to the use of KLK7 inhibitors of Formula I for the treatment and prevention of diseases, more specifically for the treatment and prevention of skin diseases. The invention also provides new compounds demonstrated to be inhibitors of KLK7.

15 Claims, 22 Drawing Sheets

(56) References Cited

OTHER PUBLICATIONS

Figure 1:
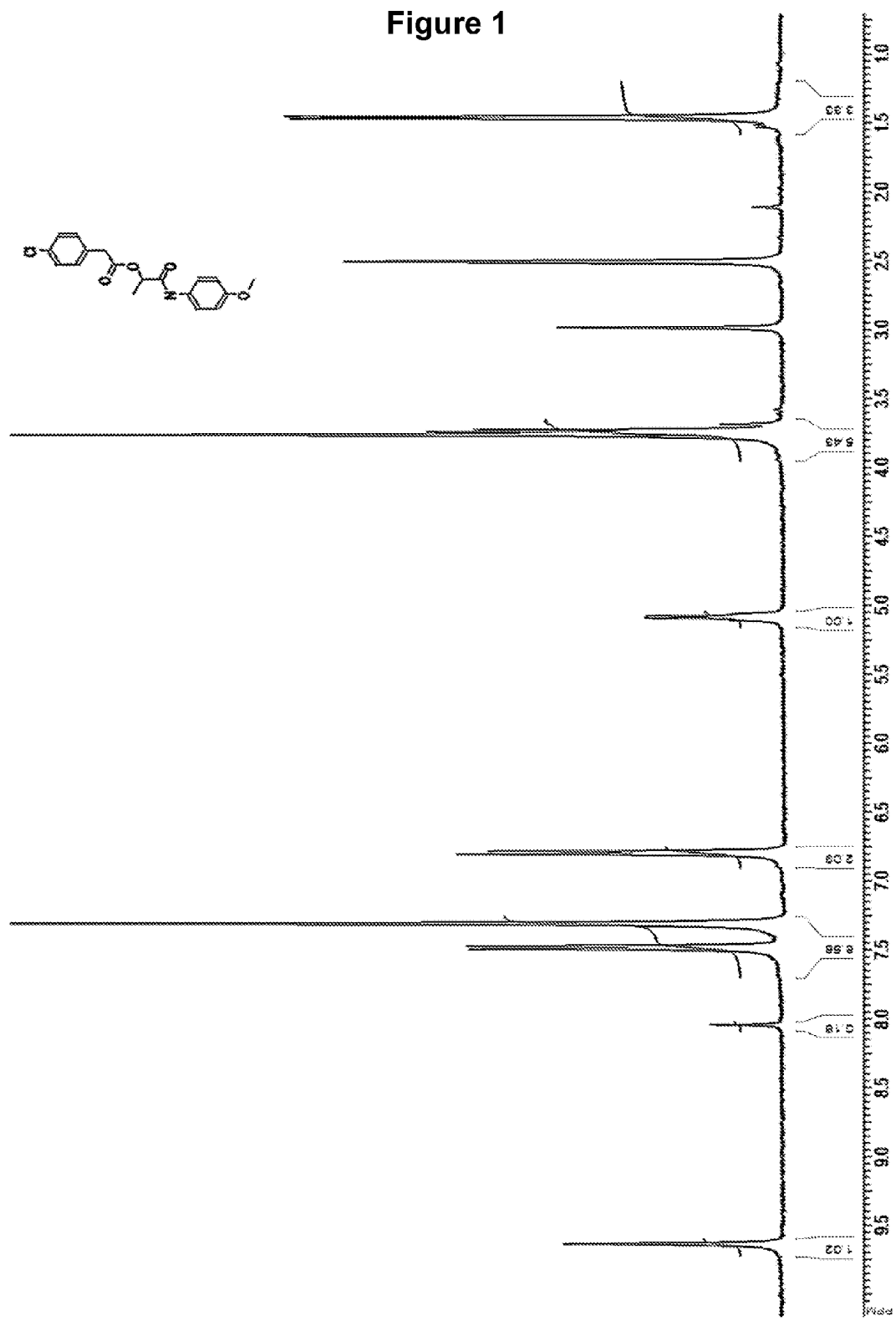

Schechter et al., "Inhibition of human kallikreins 5 and 7 by the serine protease inhibitor lympho-epithelial Kazal-type inhibitor (LEKTI)," Biol. Chem., Nov. 2005, vol. 386, pp. 1173-1184.
Franzke et al., "Antileukoprotease inhibits stratum corneum chymotryptic enzyme—Evidence for a regulative function in desquamation," The Journal of Biological Chemistry, Issue of Sep. 6, 1996, vol. 271, No. 36, pp. 21886-21890.
Descargues et al., "Spink5- deficient mice mimic Netherton syndrome through degradation of desmoglein 1 by epidermal protease hyperactivity," Nature Genetics, Jan. 2005, vol. 37, No. 1, pp. 56-65.
Walley et al., "Gene polymorphism in Netherton and common atopic disease," Nature Genetics, Oct. 2001, vol. 29, pp. 175-178.
Nishio et al., "Association between polymorphisms in the SPINK5 gene and atopic dermatitis in the Japanese," Genes Immunity, (2003), vol. 4, pp. 515-517.
Descargues et al., "Corneodesmosomal cadherins are preferential targets of stratum corneum trypsin- and chymotrypsin-like hyperactivity in Netherton syndrome," Journal of Investigative Dermatology, (2006), vol. 126, pp. 1622-1632.
Hachem et al., "Serine protease activity and residual LEKTI expression determine phenotype in Netherton syndrome," Journal of Investigative Dermatology, (2006), vol. 126, pp. 1609-1621.
Hansson et al., "Epidermal Overexpression of Stratum Corneum Chymotryptic Enzyme in Mice: A Model for Chronic Itchy Dermatitis," Journal of Investigative Dermatology, 2002, vol. 118, pp. 444-449.
Ny & Egelrud, "Transgenic mice over-expressing a serine protease in the skin: evidence of interferon gamma-independent MHC II expression by epidermal keratinocytes," Acta Derm. Venereol, 2004, vol. 84, pp. 322-327.
Ny & Egelrud, "Epidermal hyperproliferation and decreased skin barrier function in mice overexpressing stratum corneum chymotryptic enzyme," Acta Derm. Venereol, 2004, vol. 84, pp. 18-22.
Ekholm & Egelrud, "Stratum corneum chymotryptic enzyme in psoriasis," Arch. Dermatol. Res., (1999), vol. 291, pp. 195-200.
Renato F. Freitas et al., "Isomannide derivatives as new class of inhibitors for human kallikrein 7," Bioorganic & Medicinal Chemistry Letters 22, (2012), pp. 6072-6075.
International Search Report issued in International Application No. PCT/SE2015/050060 with Date of mailing May 7, 2015.
Written Opinion of the International Searching Authority issued in International Application No. PCT/SE2015/050060 with Date of mailing May 7, 2015.

KALLIKREIN 7 INHIBITORS

CROSS-REFERENCE TO RELATED APPLICATIONS

This application is a National Stage Entry of International Application No. PCT/SE2015/050060, filed on Jan. 22, 2015, and claims the benefit of and priority to SE 1430004-0, filed Jan. 23, 2014, which are hereby incorporated by reference into this application in their entirety.

FIELD OF THE INVENTION

The present invention relates to methods for inhibiting the activity of human kallikrein 7 (KLK7) (also known as serine protease stratum corneum chymotryptic enzyme, SCCE). The invention further relates to the use of KLK7 inhibitors of Formula I for the treatment and prevention of diseases, more specifically for the treatment and prevention of skin diseases. The invention also provides new compounds demonstrated to be inhibitors of KLK7.

BACKGROUND

KLK7 (hK7, or stratum corneum chymotryptic enzyme (SCCE), Swissprot P49862) is a S1 serine protease of the kallikrein gene family displaying a chymotrypsin like activity. KLK7 is mainly expressed in the skin and appears to play an important role in skin physiology (Egelrud. 1993. *Purification and preliminary characterization of stratum corneum chymotryptic enzyme: a proteinase that may be involved in desquamation.* J. Invest. Dermatol. 101, 200-204; Skytt et al. 1995. *Primary substrate specificity of recombinant human stratum corneum chymotryptic enzyme.* Biochem Biophys Res Commun 211, 586-589; Yousef et al. 2000. *The KLK7 (PRSS6) gene, encoding for the stratum corneum chymotryptic enzyme is a new member of the human kallikrein gene family—genomic characterization, mapping, tissue expression and hormonal regulation.* Gene 254, 119-1281).

KLK7 is involved in the degradation of the intercellular cohesive structure in cornified squamous epithelia in the process of desquamation. The desquamation process is well regulated and delicately balanced with the de novo production of corneocytes to maintain a constant thickness of the stratum corneum. In this regard, KLK7 is reported to be able to cleave the corneodesmosomal proteins corneodesmosin and desmocollin 1 (Simon et al. 2001. *Refined characterization of comeodesmosin proteolysis during terminal differentiation of human epidermis and its relationship to desquamation.* J. Biol. Chem. 276, 20292-20299; Caubet et al. 2004. *Degradation of corneodesmosome proteins by two serine proteases of the kallikrein family, SCTE/KLK5/hK5 and SCCE/KLK7/hK7.* J. Invest. Dermatol. 122, 1235-1244; Brattsand et al. 2005. *A proteolytic cascade of kallikreins in the stratum corneum.* J. Invest. Dermatol. 124, 198-203. In addition, it has been shown that the two lipid processing enzymes β-glucocerebrosidase and acidic sphingomyelinase can be degraded by KLK7 (Hachem et al. 2005. *Sustained serine proteases activity by prolonged increase in pH leads to degradation of lipid processing enzymes and profound alterations of barrier function and stratum corneum integrity.* J. Invest. Dermatol. 125, 510-520). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, KLK7 has been shown to activate the pro-inflammatory cytokine Pro-interleukin-1β (IL-1β) (Nylander-Lundqvist & Egelrud. 1997. *Formation of active IL-1β from pro-IL-1β catalyzed by stratum corneum chymotryptic enzyme in vitro.* Acta Derm. Venereol. 77, 203-206).

Several studies link an increased activity of KLK7 to inflammatory skin diseases like atopic dermatitis, psoriasis or Netherton syndrome. An increased KLK7 activity might lead to an uncontrolled degradation of corneodesmosomes resulting in a miss-regulated desquamation, an enhanced degradation of lipid processing enzymes resulting in a disturbed lamellar membrane architecture or an uncontrolled (in)activation of the pro-inflammatory cytokine IL-1β. It have previously been demonstrated that this could lead to an impaired skin barrier function and inflammation (WO 2004/108139).

The KLK7 activity is controlled on several levels. Various factors might be responsible for an increased KLK7 activity in inflammatory skin diseases. Firstly, the amount of protease being expressed might be influenced by genetic factors. Such a genetic link, a polymorphism in the 3'-UTR in the KLK7 gene, has been described (Vasilopoulos et al. 2004. *Genetic association between an AACC insertion in the 3'UTR of the stratum corneum chymotryptic enzyme gene and atopic dermatitis.* J. Invest. Dermatol. 123, 62-66.). The authors hypothesis that the described 4 base pair insertion in the 3'-UTR of the kallikrein 7 gene stabilizes the KLK7 mRNA and results in an overexpression of KLK7. Secondly, since KLK7 is secreted via lamellar bodies to the stratum corneum extracellular space as zymogen and it is not able to autoactivate, it needs to be activated by another protease e.g. kallikrein 5 (Caubet et al. supra). Uncontrolled activity of such an activating enzyme might result in an over-activation of KLK7. Thirdly, activated KLK7 can be inhibited by natural inhibitors like LEKTI, ALP or elafin (Schechter et al. 2005. *Inhibition of human kallikreins 5 and 7 by the serine protease inhibitor lympho-epithelial Kazal-type inhibitor (LEKTI).* Biol. Chem. 386, 1173-1184; Franzke et al. 1996. *Antileukoprotease inhibits stratum corneum chymotryptic enzyme—Evidence for a regulative function in desquamation.* J. Biol. Chem. 271, 21886-21890). The decreased expression or the lack of such inhibitors might result in an enhanced KLK7 activity.

It has been found that mutations in the spink gene, coding for LEKTI, are causative for Netherton syndrome (Descargues et al. 2005. *Spink5-deficient mice mimic Netherton syndrome through degradation of desmoglein 1 by epidermal protease hyperactivity.* Nat. Genet. 37, 56-65) and a single point mutation in the gene is linked to atopic dermatitis (Walley et al. 2001. *Gene polymorphism in Netherton and common atopic disease.* Nat. Genet. 29, 175-178; Nishio et al. 2003. *Association between polymorphisms in the SPINK5 gene and atopic dermatitis in the Japanese.* Genes Immun. 4, 515-517). Finally, another level of controlling the activity of KLK7 is the pH. KLK7 has a neutral to slightly alkaline pH optimum and there is a pH gradient from neutral to acidic from the innermost to the outermost layers in the skin. Environmental factors like soap might result in a pH increase in the outermost layers of the stratum corneum towards the pH optimum of KLK7 thereby increasing the KLK7 activity.

The hypothesis that an increased activity of KLK7 is linked to inflammatory skin diseases is supported by the following studies: Firstly, Netherton syndrome patients show a phenotype dependent increase in serine protease activity, a decrease in corneodesmosomes, a decrease in the lipid processing enzymes β-glucocerebrosidase and acidic sphingomyelinase, and an impaired barrier function (Descargues et al. 2006. *Corneodesmosomal cadherins are preferential targets of stratum corneum trypsin-and chymotrypsin-like hyperactivity in Netherton syndrome. J. Invest. Dermatol.* 126, 1622-1632; Hachem et al. 2006. *Serine protease activity and residual LEKTI expression determine phenotype in Netherton syndrome. J. Invest. Dermatol.* 126, 1609-1621.). Secondly, a transgenic mice overexpressing human kallikrein 7 shows a skin phenotype similar to that found in patients with atopic dermatitis (Hansson et al. 2002. *Epidermal Overexpression of Stratum Corneum Chymotryptic Enzyme in Mice: A Model for Chronic Itchy Dermatitis. J. Invest. Dermatol.* 118, 444-449; Ny & Egelrud. 2003. *Transgenic mice over-expressing a serine protease in the skin: evidence of interferon gamma-independent MHC II expression by epidermal keratinocytes. Acta Derm. Venereol.* 83, 322-327; Ny & Egelrud. 2004. *Epidermal hyperproliferation and decreased skin barrier function in mice overexpressing stratum corneum chymotryptic enzyme. Acta Derm. Venereol.* 84, 18-22). Thirdly, in the skin of atopic dermatitis and psoriasis patients elevated levels of KLK7 were described (Ekholm & Egelrud. 1999. *Stratum corneum chymotryptic enzyme in psoriasis. Arch. Dermatol. Res.* 291, 195-200). Therefore, KLK7 is considered to be a target for the treatment of inflammatory skin diseases like atopic dermatitis, psoriasis or Netherton syndrome and there is a need for specific inhibitors thereof.

WO 2004/108139 describes certain substituted benzoxazinone and thienoxazinone compounds as inhibitors of KLK7.

WO 2009/000878 describes substituted pyrrolidine-1,2-dicarboxamide compounds as inhibitors of KLK7.

WO 2009/024527 and WO 2009/024528 describe cyclic depsipeptides as inhibitors of KLK7.

DESCRIPTION OF THE INVENTION

The present inventors have now been found that the activity of KLK7 can be inhibited by compounds according to Formula I.

Accordingly, the present invention provides a compound according to Formula I

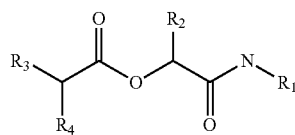

Formula I wherein $R_1$ is selected from aryl, substituted aryl, heteroaryl, and substituted heteroaryl;
$R_2$ is selected from hydrogen, alkyl, substituted alkyl, aryl, and substituted aryl;
$R_3$ is selected from alkyl, substituted alkyl, cycloalkyl, substituted cycloalkyl, aryl, substituted aryl, heteroaryl, substituted heteroaryl, and —$C_1$-$C_3$-alkyl-$R_5$, wherein $R_5$ is selected from cycloalkyl, substituted cycloalkyl, aryl, substituted aryl, heteroaryl, substituted heteroaryl;
$R_4$ is selected from hydrogen, alkyl, substituted alkyl, aryl, substituted aryl, heteroaryl, and substituted heteroaryl, and —NH—CO—$R_6$, wherein $R_6$ is selected from aryl, and substituted aryl, heteroaryl, and substituted heteroaryl;
or a pharmaceutical acceptable salt thereof,
for use in medicine, more specifically for use in the prophylaxis, prevention and/or treatment of a skin disease.

Preferably, $R_1$ is selected from phenyl, substituted phenyl, isoxazolyl, substituted isoxazolyl and heteroaryl.

Preferably, $R_2$ is selected from hydrogen, —$C_1$-$C_6$-alkyl, $C_1$-$C_3$-alkyloxy-$C_1$-$C_6$-alkyl, and phenyl.

Preferably, $R_3$ is selected from alkyl, substituted alkyl, cycloalkyl, substituted cycloalkyl, aryl, substituted aryl, and —$C_1$-$C_3$-alkyl-$R_5$, wherein $R_5$ preferably is selected from cycloalkyl, substituted cycloalkyl, aryl, and substituted aryl.

Preferably, $R_4$ is selected from hydrogen, alkyl, substituted alkyl, aryl, substituted aryl, and —NH—CO—$R_6$, wherein $R_6$ preferably is selected from aryl, and substituted aryl.

The stereochemical configuration around the carbon which is covalently bound to $R_2$ can be (S) or (R). Preferably, the stereochemical configuration around the carbon which is covalently bound to $R_2$ is (S).

The invention further relates to the use of a compound according to the Formula I or a pharmaceutically acceptable salt thereof, for the manufacture of a medicament for the treatment of a skin disease.

The skin disease may be an inflammatory skin disease. The skin disease can be selected from Netherton syndrome, atopic dermatitis, contact dermatitis, eczema, psoriasis, acne, epidermal hyperkeratosis, acanthosis, epidermal inflammation, dermal inflammation and pruritus.

The subject to be treated can be a mammal, such as a human, a dog, a cat, or a horse.

The present invention further provides a method for the prophylaxis, prevention and/or treatment of a skin disease which comprises the administration of a therapeutically active amount of a compound according to Formula I

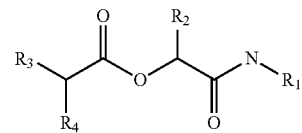

Formula I wherein $R_1$ is selected from aryl, substituted aryl, heteroaryl, and substituted heteroaryl;
$R_2$ is selected from hydrogen, alkyl, substituted alkyl, aryl, and substituted aryl;
$R_3$ is selected from alkyl, substituted alkyl, cycloalkyl, substituted cycloalkyl, aryl, substituted aryl, heteroaryl, substituted heteroaryl, and —$C_1$-$C_3$-alkyl-$R_5$, wherein $R_5$ is selected from cycloalkyl, substituted cycloalkyl, aryl, substituted aryl, heteroaryl, substituted heteroaryl;
$R_4$ is selected from hydrogen, alkyl, substituted alkyl, aryl, substituted aryl, heteroaryl, substituted heteroaryl, and —NH—CO—$R_6$, wherein $R_6$ is selected from aryl, and substituted aryl, heteroaryl, and substituted heteroaryl;
to a subject in need of such treatment.

The skin disease may be an inflammatory skin disease. The skin disease can be selected from Netherton syndrome, atopic dermatitis, contact dermatitis, eczema, psoriasis, acne, epidermal hyperkeratosis, acanthosis, epidermal inflammation, dermal inflammation and pruritus.

The subject to be treated can be a mammal, such as a human, a dog, a cat, or a horse.

The present invention further provides a cosmetic or skin care composition comprising at least one compound with the Formula I, or a pharmaceutically acceptable salt thereof, said composition being in a form suitable for topical administration, and selected from the group consisting of a cream, an ointment, a lotion, a liniment, a gel, a paste, a stick, a spray, a shampoo, a soap, a hair conditioner and a powder.

The invention further provides the use of a compound according to Formula I, or a pharmaceutically acceptable salt thereof, for treatment or prophylaxis of cosmetic skin conditions.

The present invention further provides compounds according to Formula I

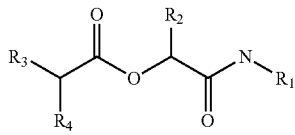

Formula I wherein the compounds are selected from
(1) [1-methyl-2-[(5-methylisoxazol-3-yl)amino]-2-oxo-ethyl] 2-(4-chlorophenyl) acetate
(3) 1-[(5-methylisoxazol-3-yl)carbamoyl]propyl 2-(4-chlorophenyl) acetate
(7) [1-methyl-2-[(5-methylisoxazol-3-yl)amino]-2-oxo-ethyl] 2-(4-methoxyphenyl) acetate
(12) 1-[(5-methylisoxazol-3-yl)carbamoyl]propyl 2-(4-methoxyphenyl) acetate
(14) [1-methyl-2-[(5-methylisoxazol-3-yl)amino]-2-oxo-ethyl] 3-cyclopentylpropanoate
(15) [2-(4-methoxyanilino)-1-methyl-2-oxo-ethyl] 2-(4-methoxyphenyl)acetate
(16) 1-[(5-methylisoxazol-3-yl)carbamoyl]propyl 3-cyclopentylpropanoate
(17) [2-[(5-methylisoxazol-3-yl)amino]-2-oxo-1-phenyl-ethyl] 2-(4-chlorophenyl)acetate
(20) [2-[(5-methylisoxazol-3-yl)amino]-2-oxo-1-phenyl-ethyl] 3-cyclopentylpropanoate
(23) 1-[(5-methylisoxazol-3-yl)carbamoyl]propyl 2-(4-methoxyphenyl)acetate
(26) 1-[(5-methylisoxazol-3-yl)carbamoyl]propyl 2-(1,3-benzodioxol-5-yl)acetate
(36) [2-[(5-methylisoxazol-3-yl)amino]-2-oxo-1-phenyl-ethyl] 2-(4-methoxyphenyl) acetate
(39) 1-[(5-methylisoxazol-3-yl)carbamoyl]propyl 2-(3,4-dichlorophenyl)acetate
(41) 1-[(5-methylisoxazol-3-yl)carbamoyl]propyl 2-(3,4-dimethoxyphenyl)acetate
(47) [1-methyl-2-[(5-methylisoxazol-3-yl)amino]-2-oxo-ethyl] 2,2-diphenylacetate
(49) [2-[(5-methylisoxazol-3-yl)amino]-2-oxo-1-phenyl-ethyl] 2-benzamido-2-phenyl-acetate
(52) [1-methyl-2-[(5-methylisoxazol-3-yl)amino]-2-oxo-ethyl] 2-benzamido-2-phenyl-acetate
(54) [2-[(5-methylisoxazol-3-yl)amino]-2-oxo-1-phenyl-ethyl] 2,2-diphenylacetate
(60) [2-[(5-methylisoxazol-3-yl)amino]-2-oxo-ethyl] 2-benzamido-2-phenyl-acetate
(70) [2-methyl-1-[(5-methylisoxazol-3-yl)carbamoyl]propyl] 2-(4-chlorophenyl)acetate
(72) [2-methyl-1-[(5-methylisoxazol-3-yl)carbamoyl]propyl] 3-cyclopentylpropanoate
(75) [2-methyl-1-[(5-methylisoxazol-3-yl)carbamoyl]propyl] 2-benzamido-2-phenyl-acetate
(79) [2-methyl-1-[(5-methylisoxazol-3-yl)carbamoyl]propyl] 2,2-diphenylacetate
(81) [2-[(5-methylisoxazol-3-yl)amino]-2-oxo-ethyl] 2-(4-chlorophenyl)acetate
(84) [2-methyl-1-[(5-methylisoxazol-3-yl)carbamoyl]propyl] 2-(4-methoxyphenyl)acetate The present invention further provides compounds according to Formula I

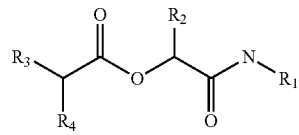

Formula I wherein the compounds are selected from
(4) [2-(4-methoxyanilino)-1-methyl-2-oxo-ethyl] 2-(4-chlorophenyl)acetate
(6) 1-[(4-methoxyphenyl)carbamoyl]propyl 2-(4-chlorophenyl)acetate
(8) 1-[(4-fluorophenyl)carbamoyl]propyl 2-(4-chlorophenyl)acetate
(9) 1-(phenylcarbamoyl)propyl 2-(4-chlorophenyl)acetate
(10) [2-(4-methoxyanilino)-1-methyl-2-oxo-ethyl] 3-cyclopentylpropanoate
(11) 1-[(4-methoxyphenyl)carbamoyl]propyl 3-cyclopentylpropanoate
(13) [2-(4-methoxyanilino)-2-oxo-1-phenyl-ethyl] 2-(4-chlorophenyl)acetate
(19) [2-(4-methoxyanilino)-2-oxo-1-phenyl-ethyl] 3-cyclopentylpropanoate
(24) 1-[(4-methoxyphenyl)carbamoyl]propyl 2-(4-methoxyphenyl)acetate
(25) 1-[(4-fluorophenyl)carbamoyl]propyl 3-cyclopentylpropanoate
(30) 1-[(4-fluorophenyl)carbamoyl]propyl 2-(4-methoxyphenyl)acetate
(31) (2-anilino-1-methyl-2-oxo-ethyl) 3-cyclopentylpropanoate
(32) (2-anilino-2-oxo-1-phenyl-ethyl) 2-(4-chlorophenyl)acetate
(34) 1-(phenylcarbamoyl)propyl 2-(4-methoxyphenyl)acetate
(35) [2-(4-methoxyanilino)-2-oxo-1-phenyl-ethyl] 2-(4-methoxyphenyl)acetate
(37) [2-(benzylamino)-2-oxo-1-phenyl-ethyl] 3-cyclopentylpropanoate
(42) [2-(4-methoxyanilino)-2-oxo-ethyl] 2-(4-methoxyphenyl)acetate
(43) 1-[(4-methoxyphenyl)carbamoyl]propyl 2,2-diphenylacetate
(44) 1-[(4-fluorophenyl)carbamoyl]propyl 2,2-diphenylacetate
(48) 1-(phenylcarbamoyl)propyl 2,2-diphenylacetate
(59) [2-(4-methoxyanilino)-2-oxo-ethyl] 2-benzamido-2-phenyl-acetate
(61) [2-(4-fluoroanilino)-2-oxo-ethyl] 2-benzamido-2-phenyl-acetate
(62) (2-anilino-2-oxo-ethyl) 2-benzamido-2-phenyl-acetate

(64) 1-[(4-methoxyphenyl)carbamoyl]propyl 2-benzamido-2-phenyl-acetate
(65) 1-[(4-fluorophenyl)carbamoyl]propyl 2-benzamido-2-phenyl-acetate
(66) (2-anilino-1-methyl-2-oxo-ethyl) 2-benzamido-2-phenyl-acetate
(71) [2-(4-methoxyanilino)-1-methyl-2-oxo-ethyl] 2-benzamido-2-phenyl-acetate
(76) (2-anilino-2-oxo-1-phenyl-ethyl) 2-benzamido-2-phenyl-acetate
(78) [2-(4-methoxyanilino)-2-oxo-1-phenyl-ethyl] 2,2-diphenylacetate
(83) [2-(benzylamino)-1-methyl-2-oxo-ethyl] 2-benzamido-2-phenyl-acetate
(91) [2-methyl-1-(phenylcarbamoyl)propyl] 2-(4-chlorophenyl)acetate
(92) [1-[(4-methoxyphenyl)carbamoyl]-2-methyl-propyl] 2-(4-chlorophenyl)acetate
(93) [2-methyl-1-(phenylcarbamoyl)propyl] 2-benzamido-2-phenyl-acetate
(94) [2-methyl-1-(phenylcarbamoyl)propyl] 2-(4-methoxyphenyl)acetate
(95) [1-[(4-methoxyphenyl)carbamoyl]-2-methyl-propyl] 2-benzamido-2-phenyl-acetate
(96) [1-[(4-fluorophenyl)carbamoyl]-2-methyl-propyl] 2-benzamido-2-phenyl-acetate The stereochemical configuration around the carbon which is covalently bound to $R_2$ of the compounds according to the invention can be (S) or (R). Preferably, the stereochemical configuration around the carbon which is covalently bound to $R_2$ of the compounds according to the invention is (S).

The invention further provides pharmaceutical compositions comprising a compound according to the invention in admixture with pharmaceutically acceptable adjuvants, diluents and/or carriers.

The invention further provides a compound according to the invention for use in medicine.

The invention further provides a compound or a pharmaceutical composition according to the invention for use in prophylaxis, prevention and/or treatment of skin diseases. The skin disease can be an inflammatory skin disease. The inflammatory skin disease can be selected from Netherton syndrome, atopic dermatitis, contact dermatitis, eczema, psoriasis, acne, epidermal hyperkeratosis, acanthosis, epidermal inflammation, dermal inflammation and pruritus.

As will be understood, the compounds of Formula I described herein are effective KLK7 inhibitors. However, as some variation in the inhibition efficiency between the individual compounds of Formula I may be present, the inventors have provided suitable preliminary assays which can be used in order to assess the inhibition efficiency of the compounds of Formula I. For example, the "KLK7 Inhibitor Test" described in Example 1 herein is a simple test which may be performed to initially assess the potency of the compound. Accordingly, a compound of Formula I which is preferred for the methods and uses disclosed herein, is a compound which, when assayed in the "KLK7 Inhibitor Test" described herein, has an $IC_{50}$ value of less than 10 µM. More preferably, the compound has an $IC_{50}$ value of less than 5 µM, even more preferably the compound has an $IC_{50}$ value of less than 3 µM, still more preferably the compound has an $IC_{50}$ value of less than 2 µM such as an $IC_{50}$ value of less than 1 µM, most preferably the compound has an $IC_{50}$ value of less than 0.5 µM, such as an $IC_{50}$ value of less than 0.1 µM, when assayed in the "KLK7 Inhibitor Test" described herein.

LEGENDS TO FIGURES

Figure 2:
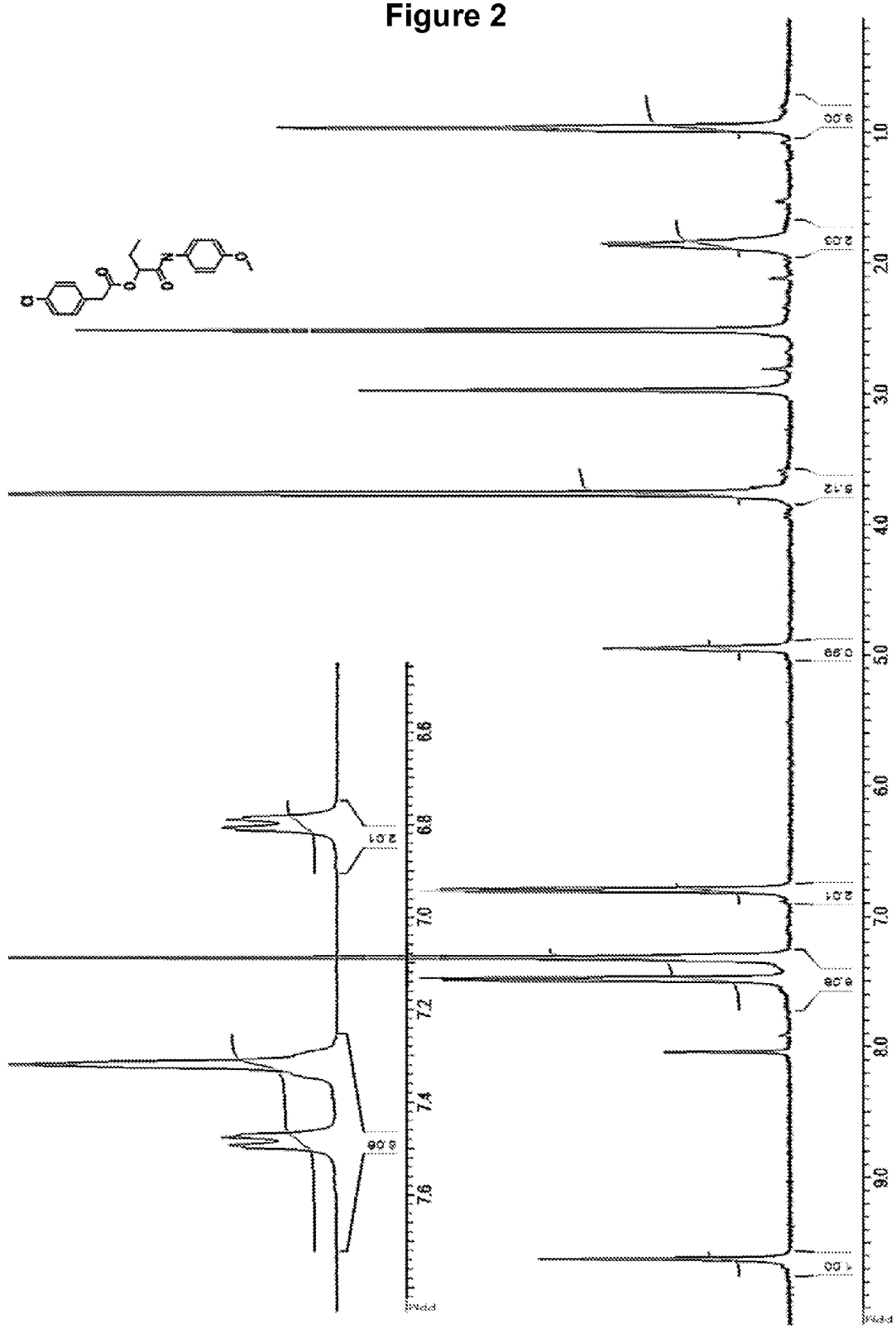
Figure 3:
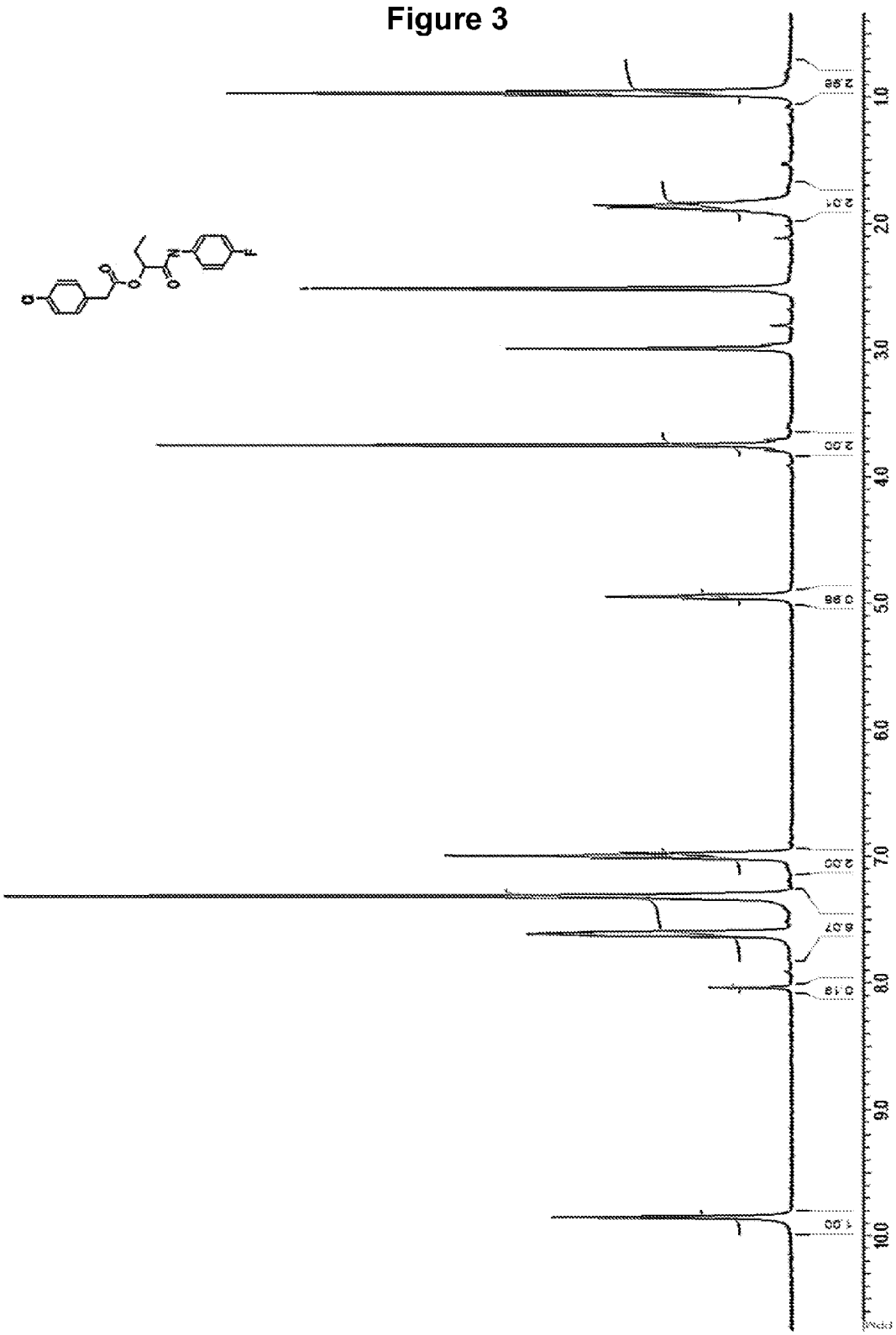
Figure 4:
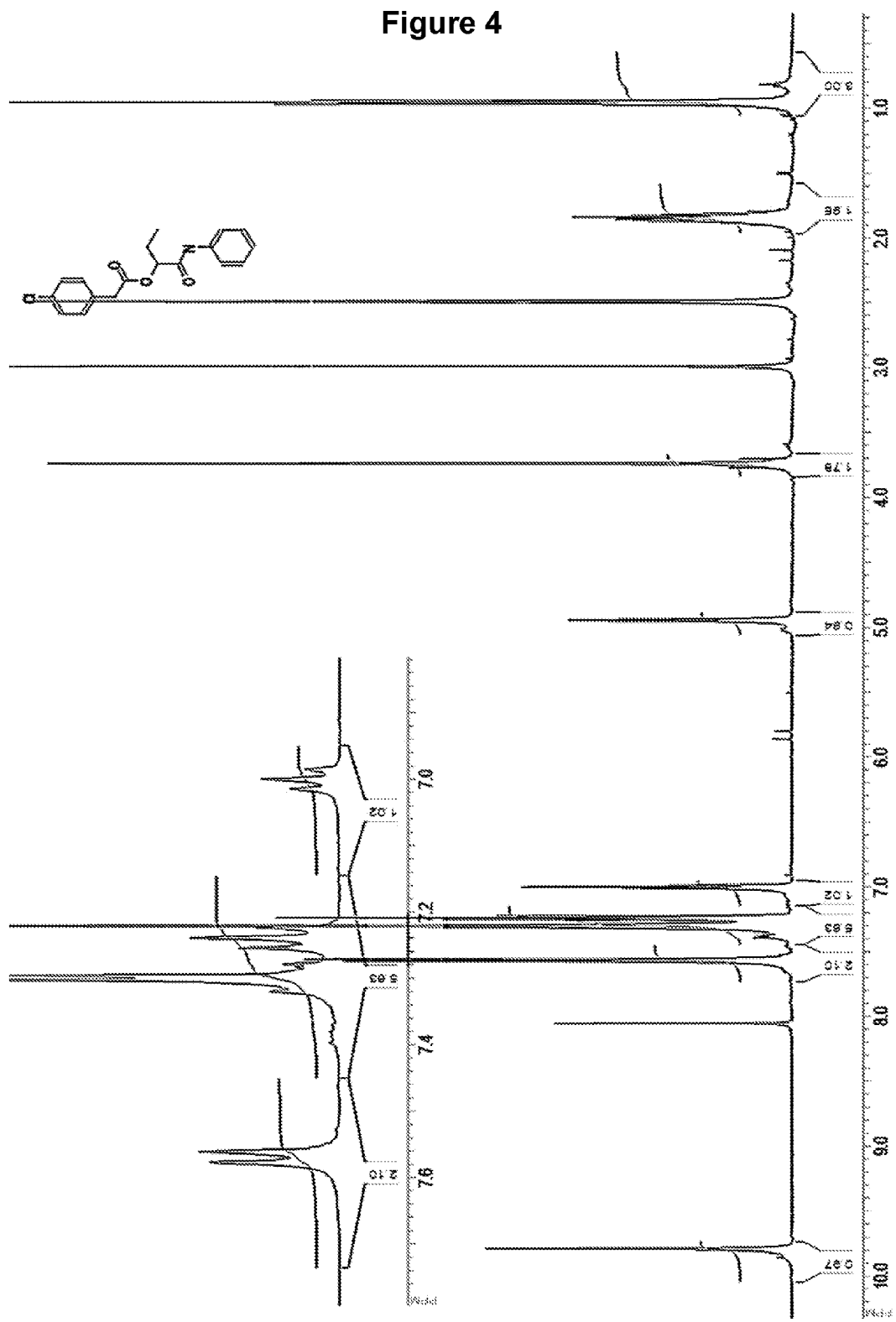
Figure 5:
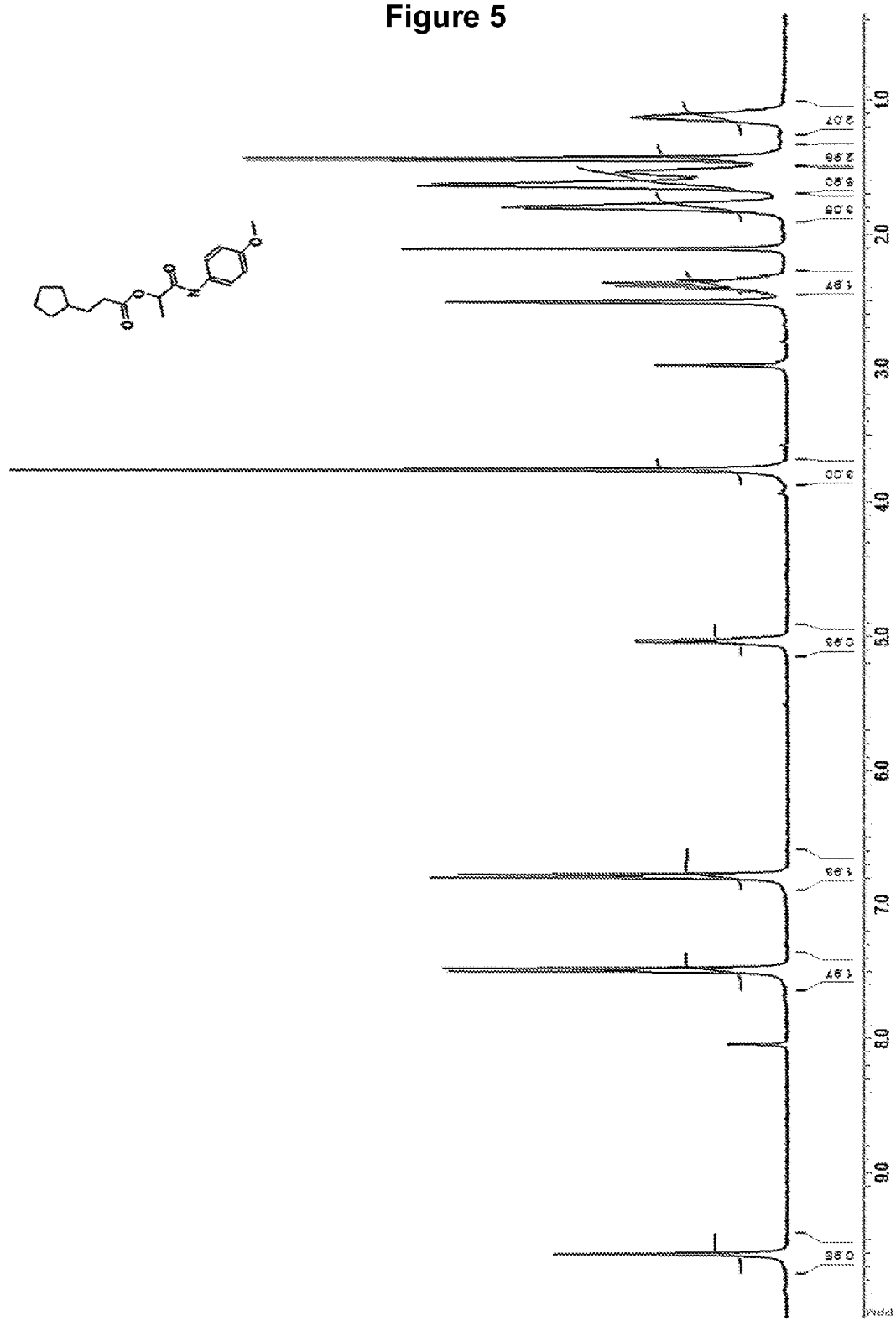
Figure 6:
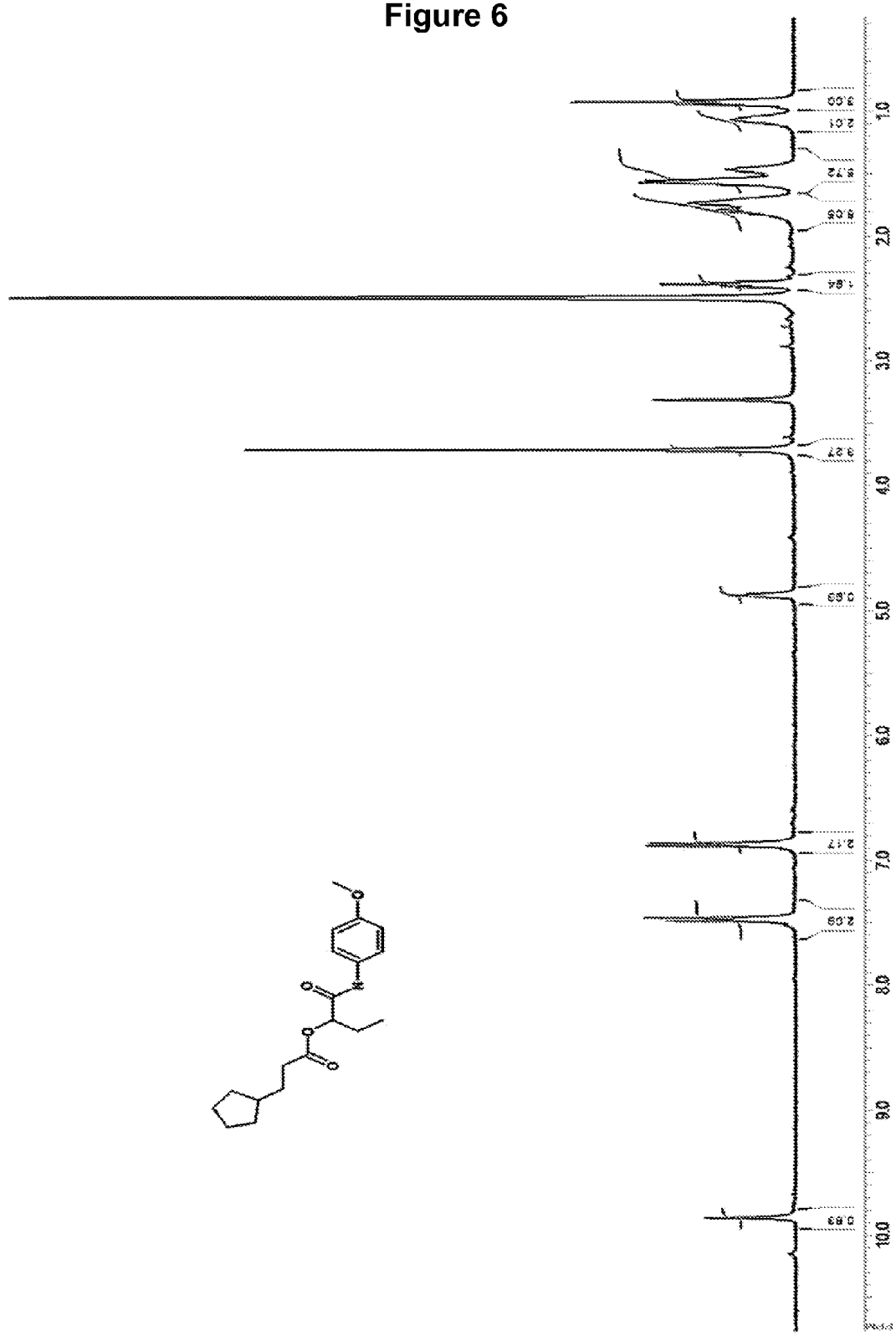
Figure 7:
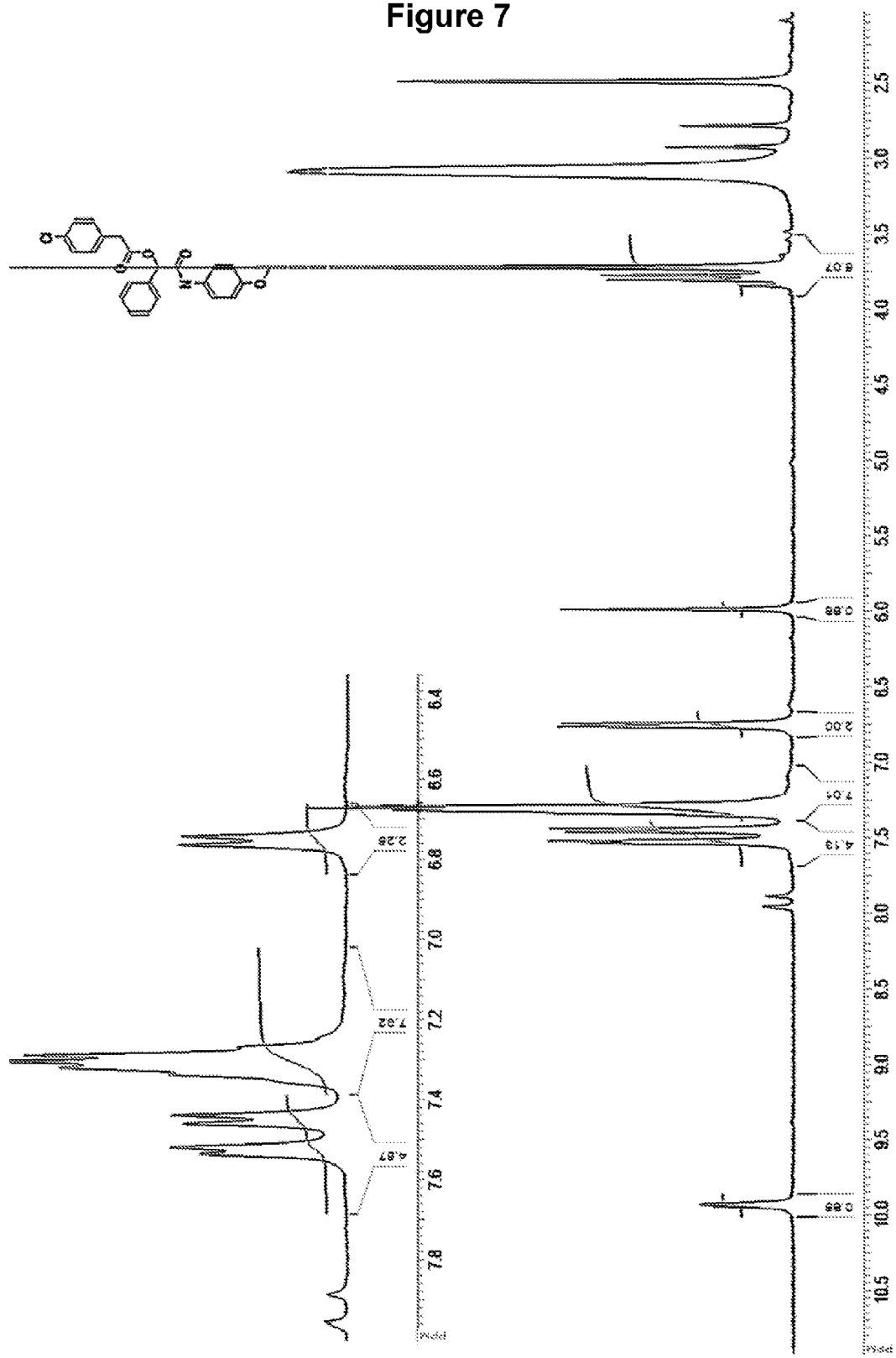
Figure 8:
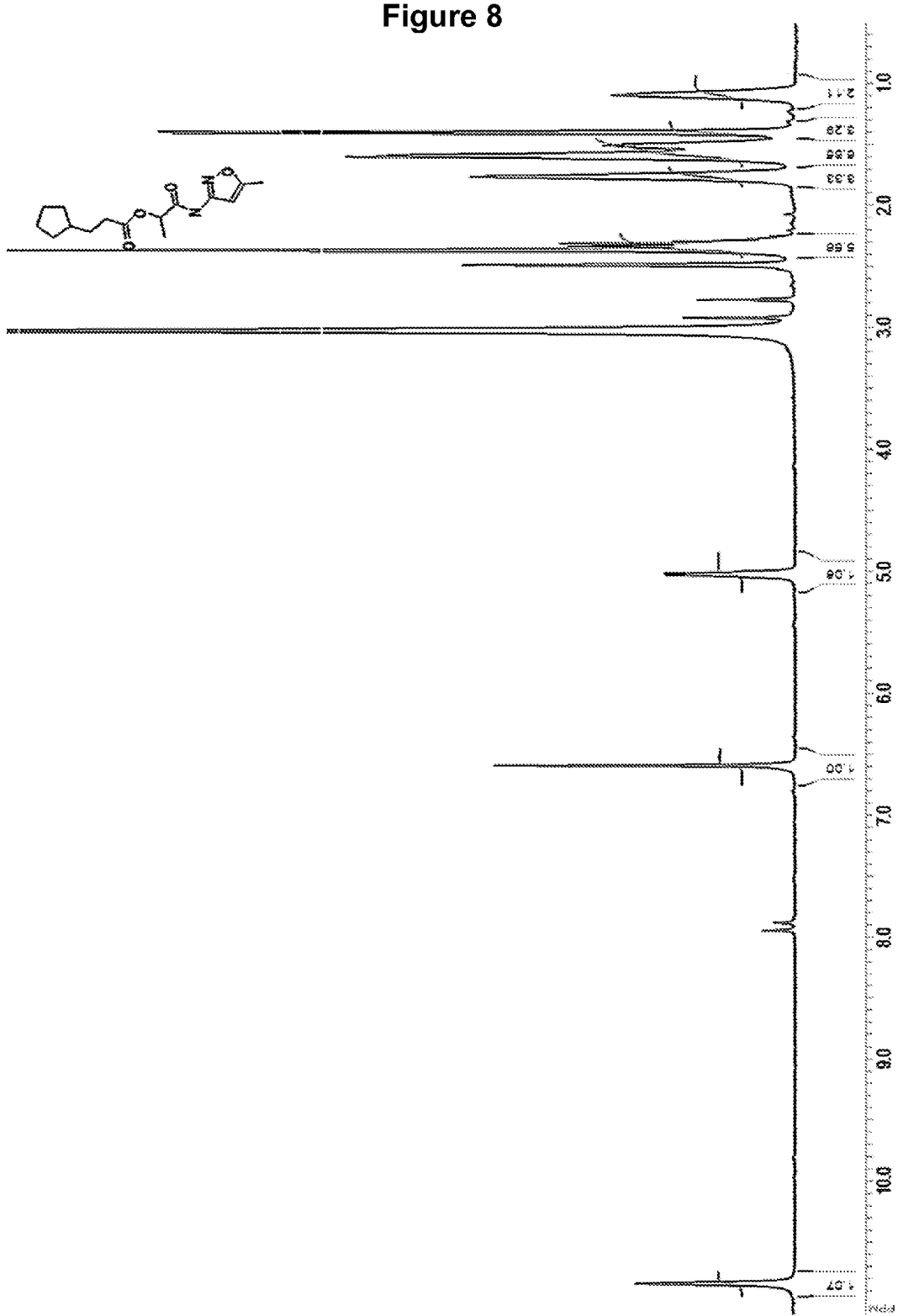
Figure 9:
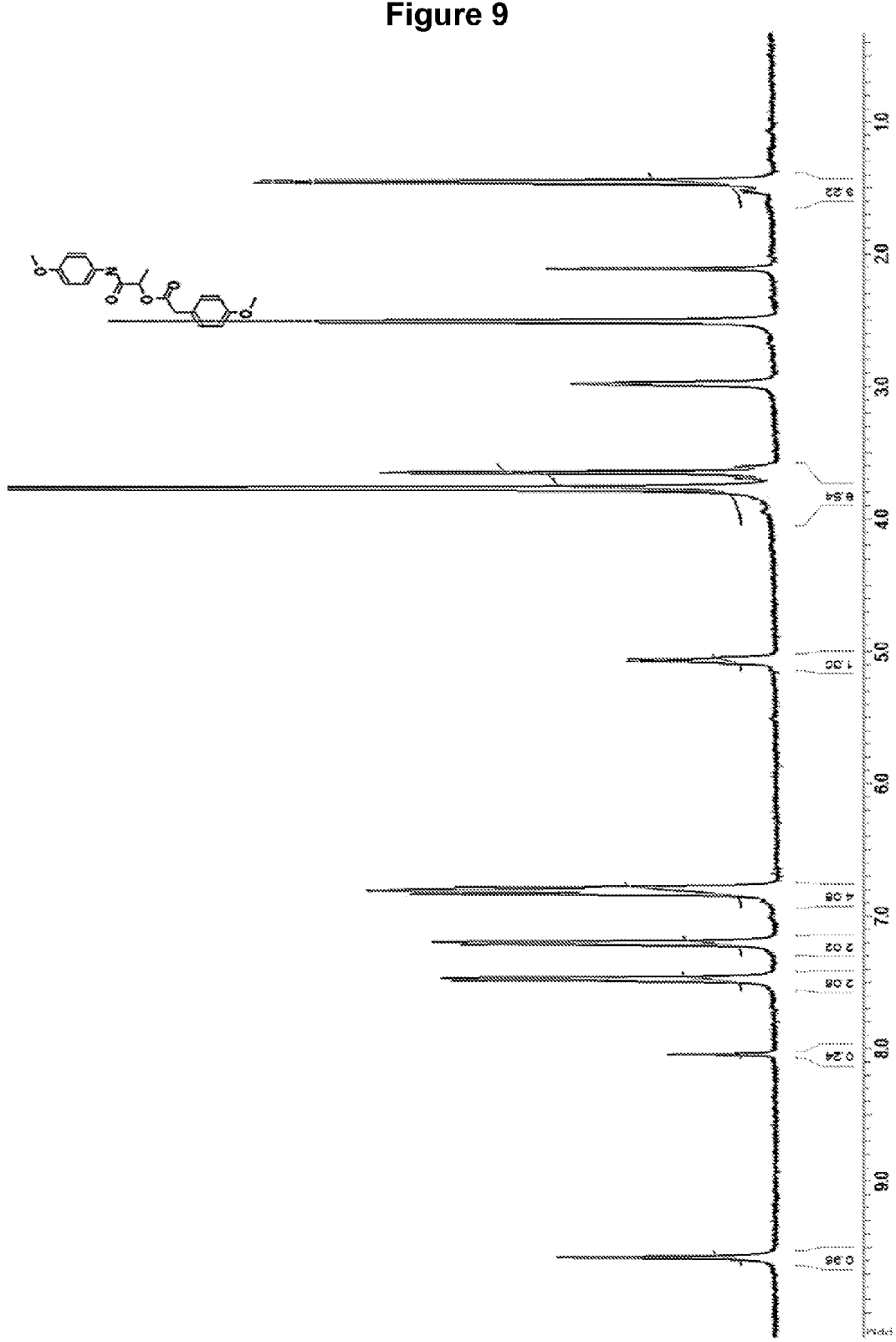
Figure 10:
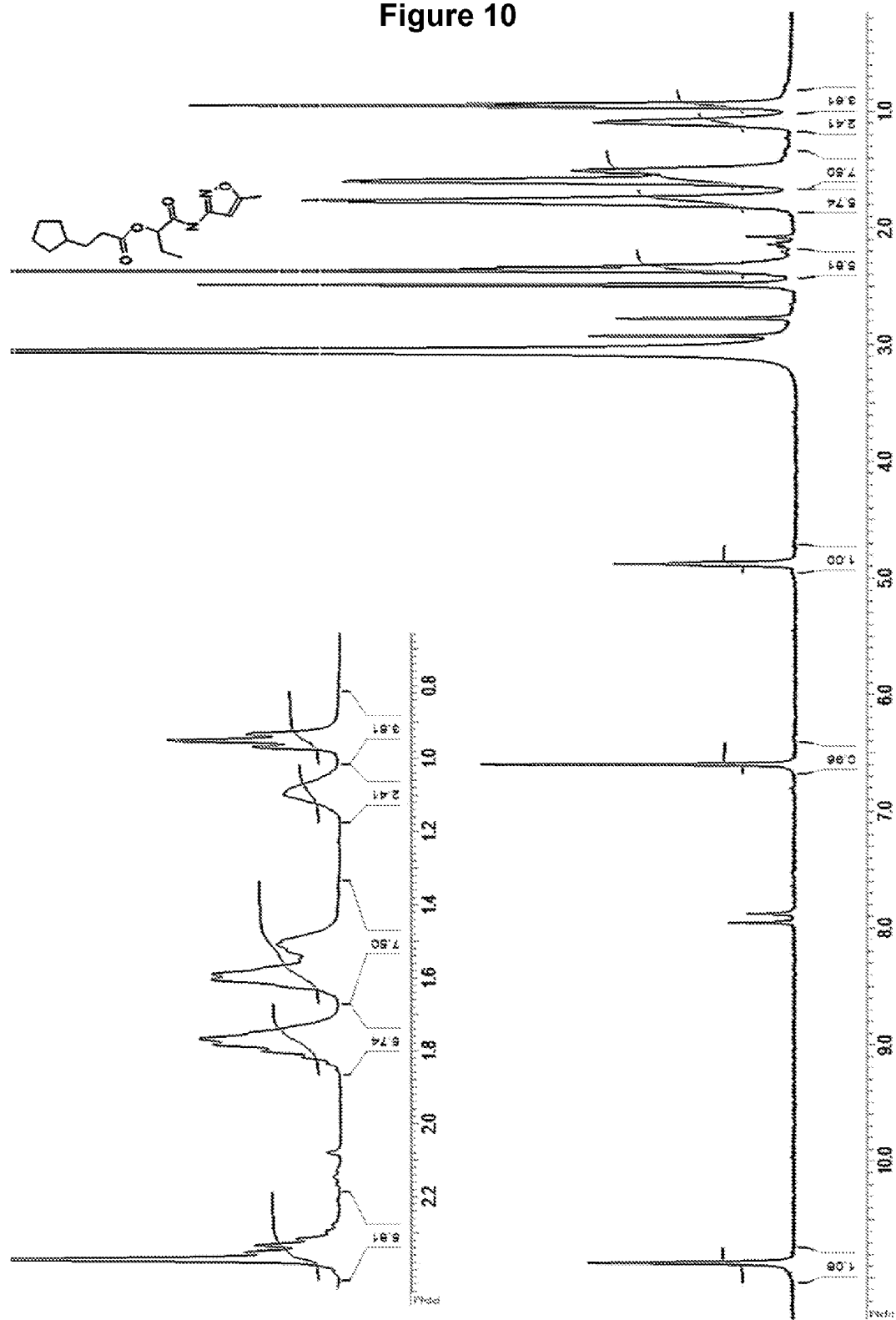
Figure 11:
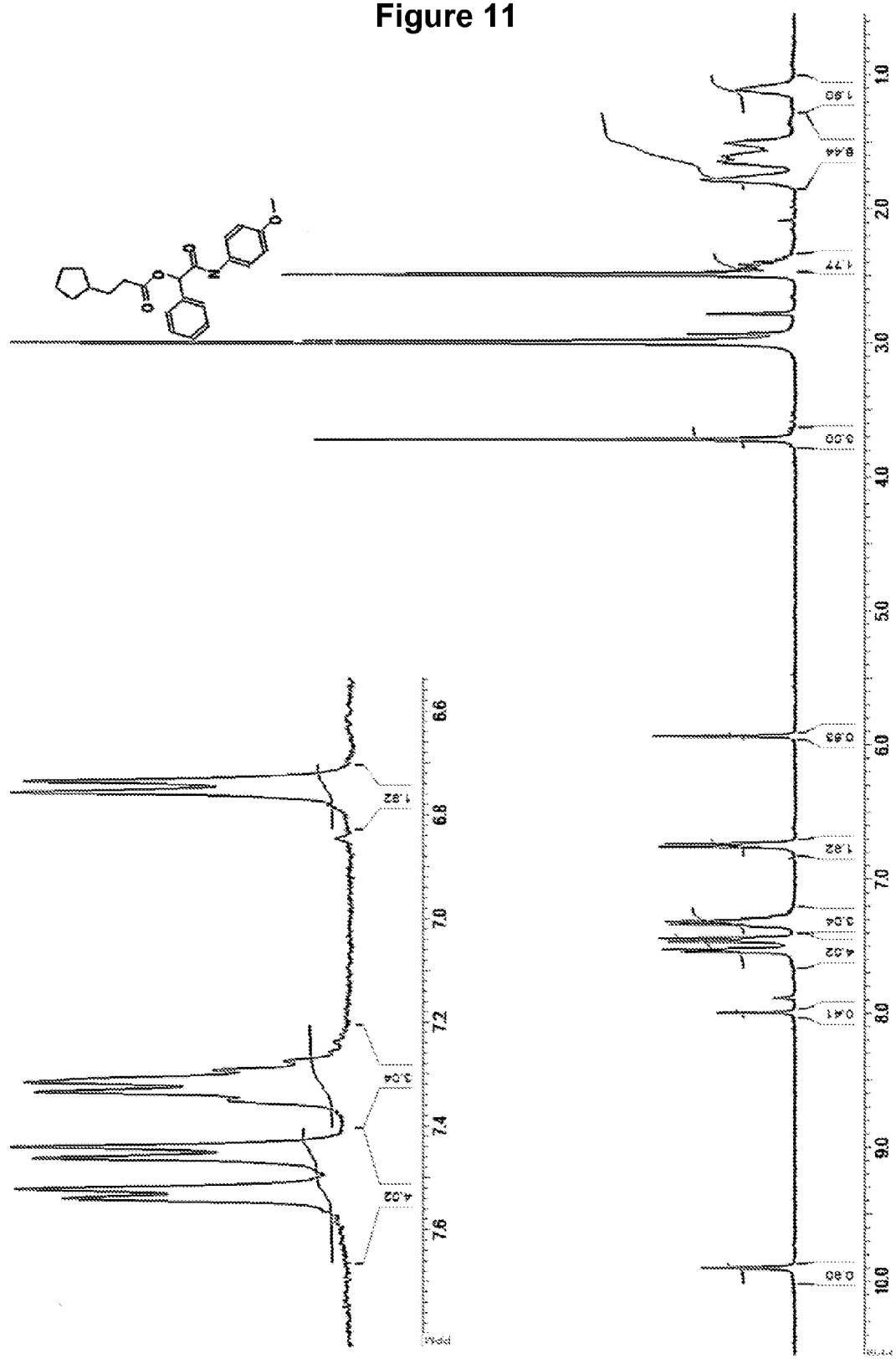
Figure 12:
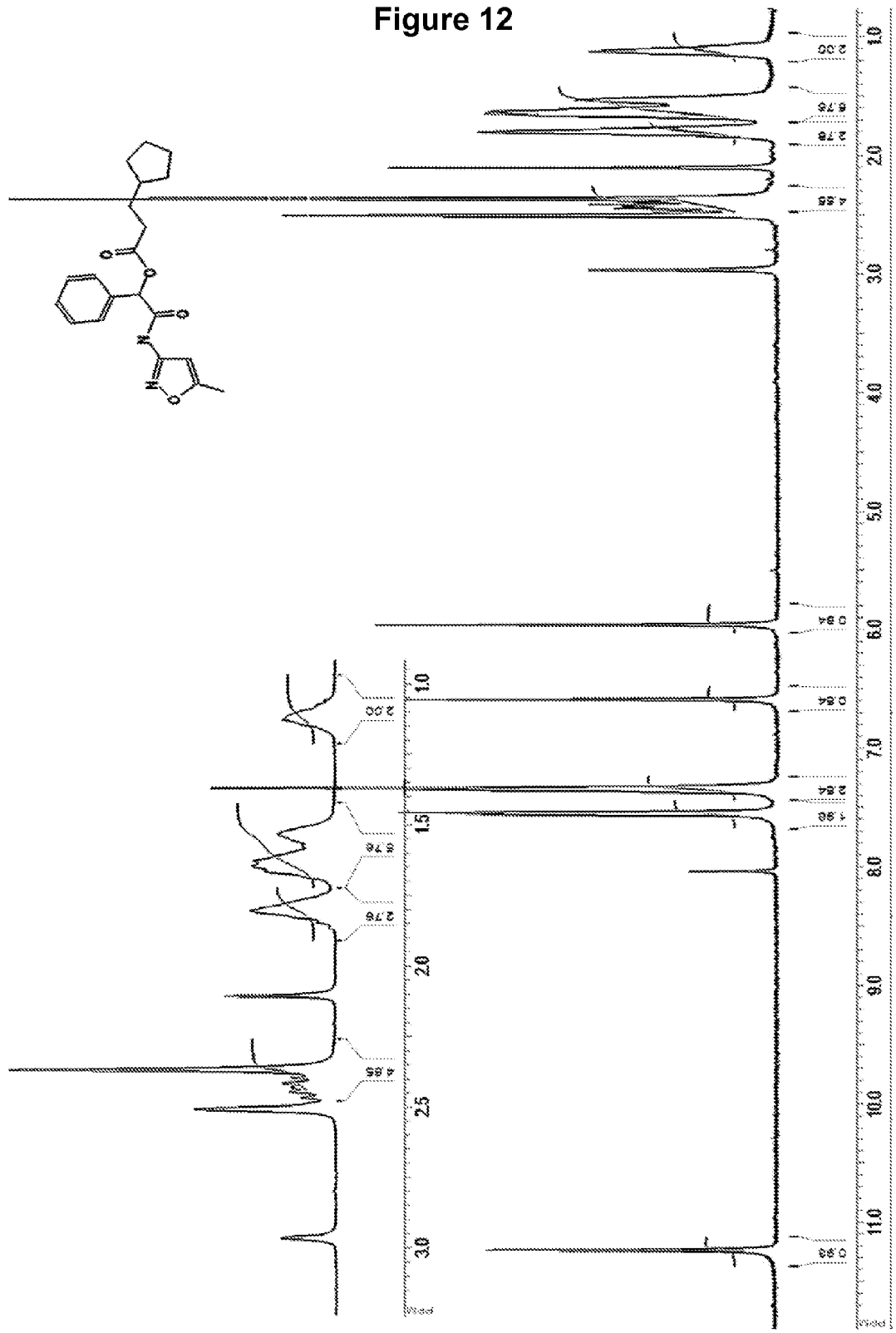
Figure 13:
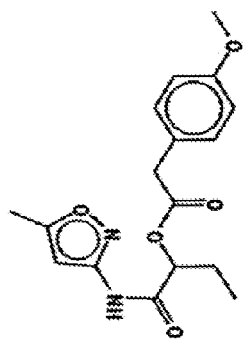
Figure 13:
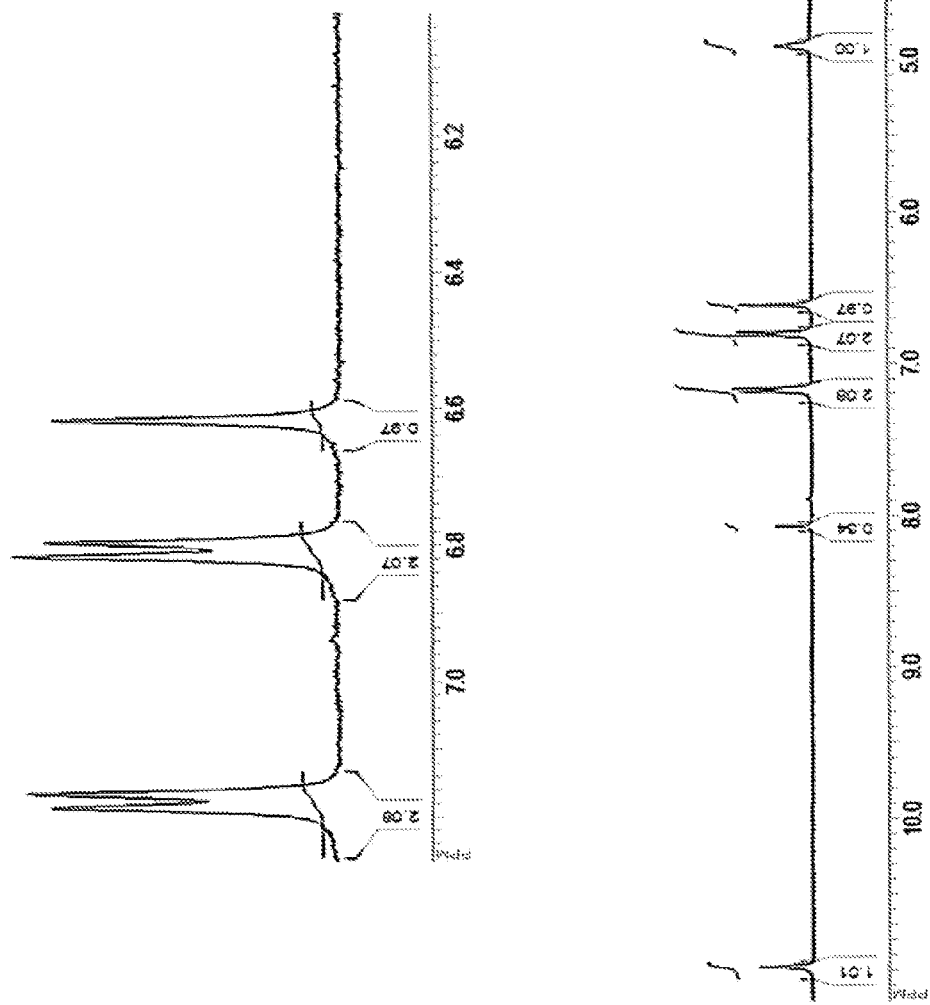
Figure 14:
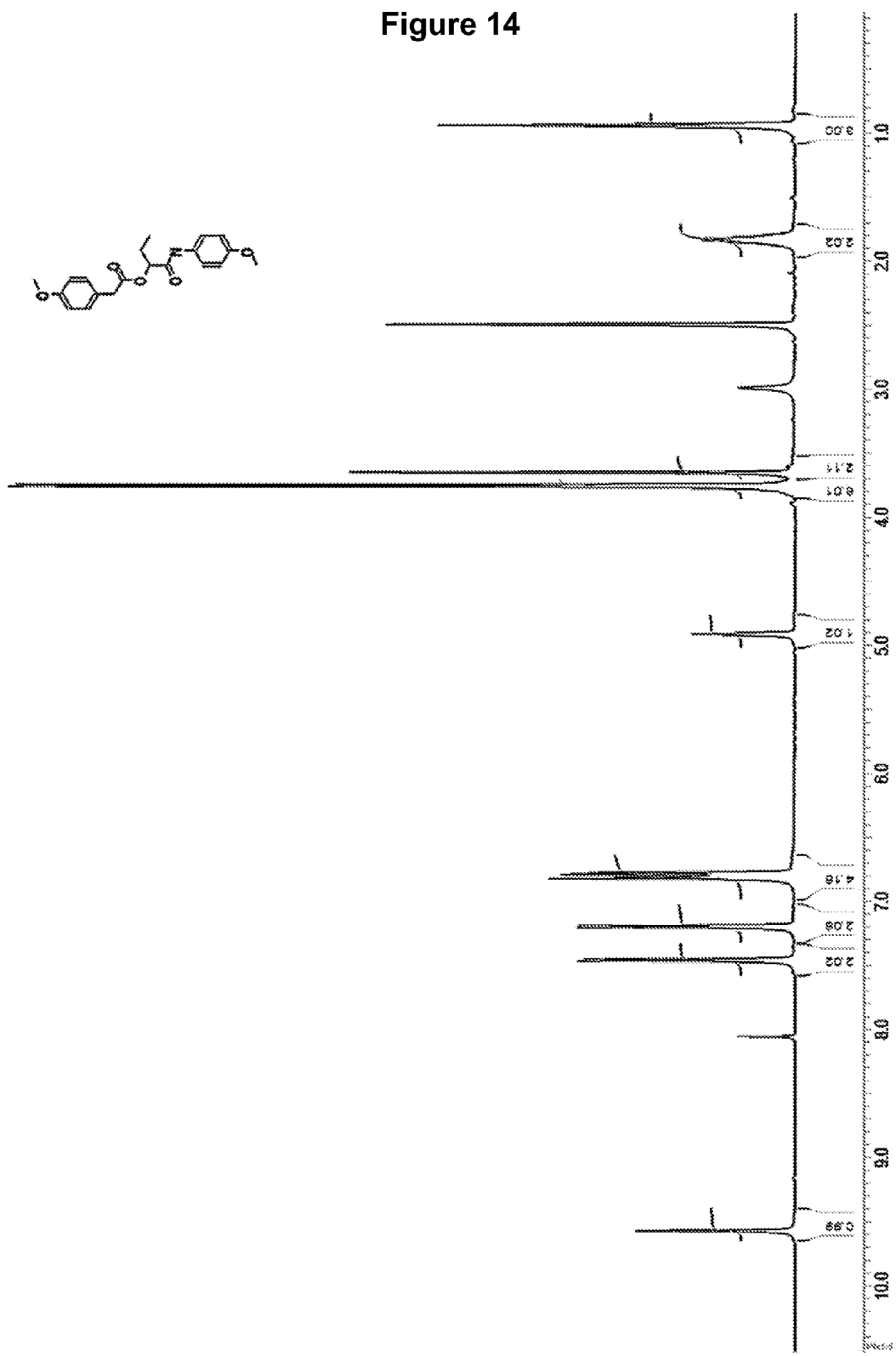
Figure 15:
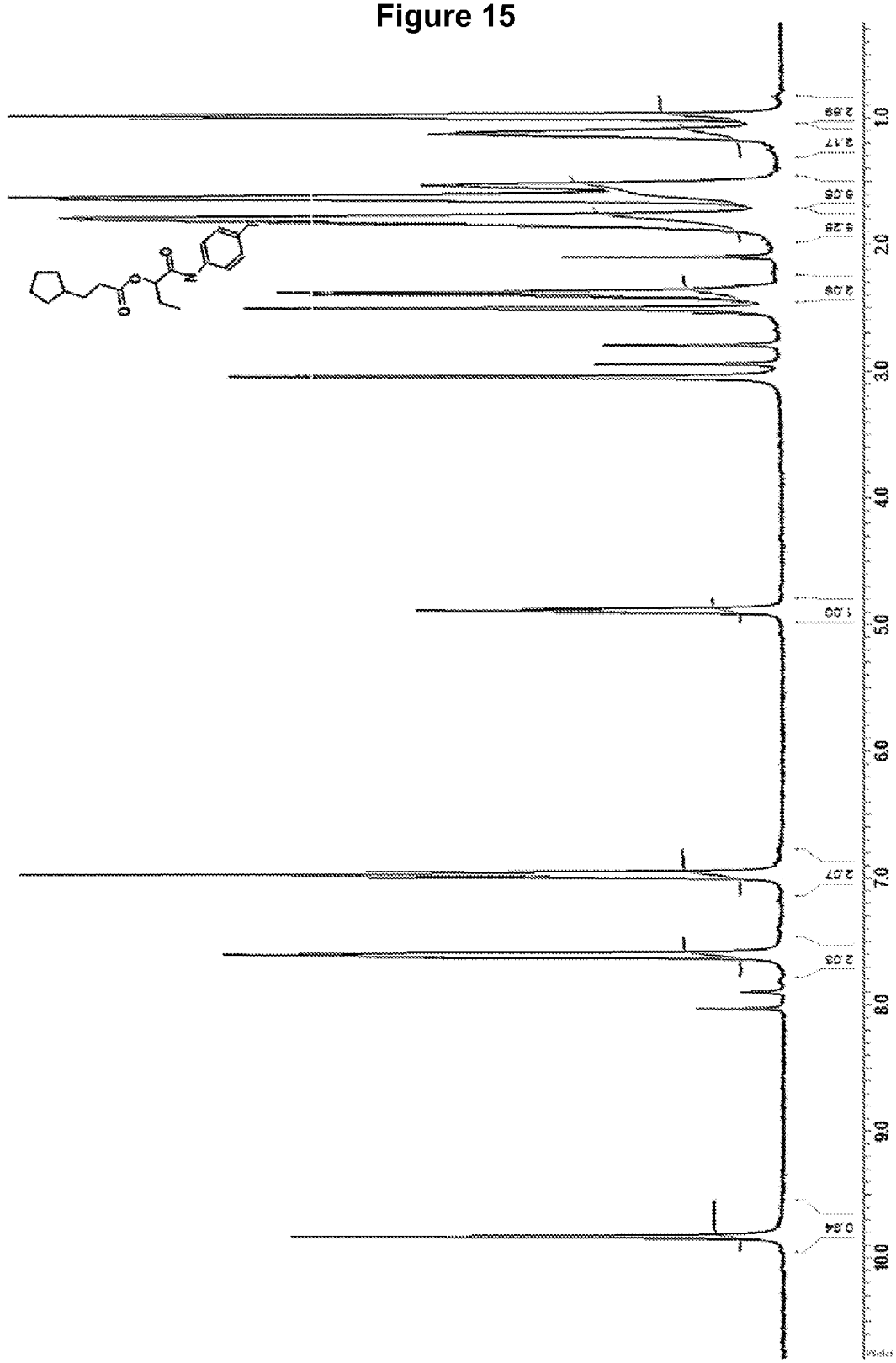
Figure 16:
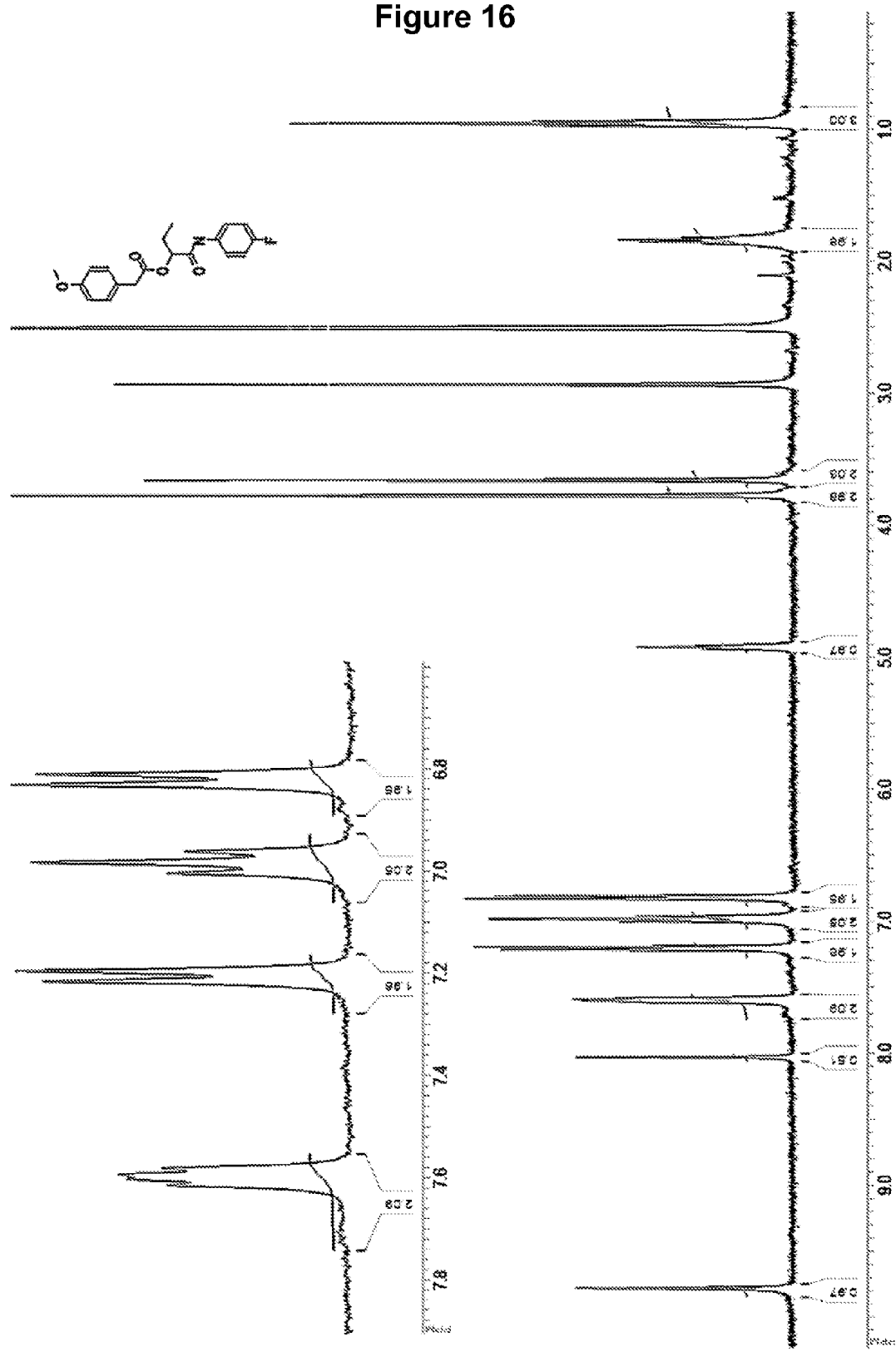
Figure 17:
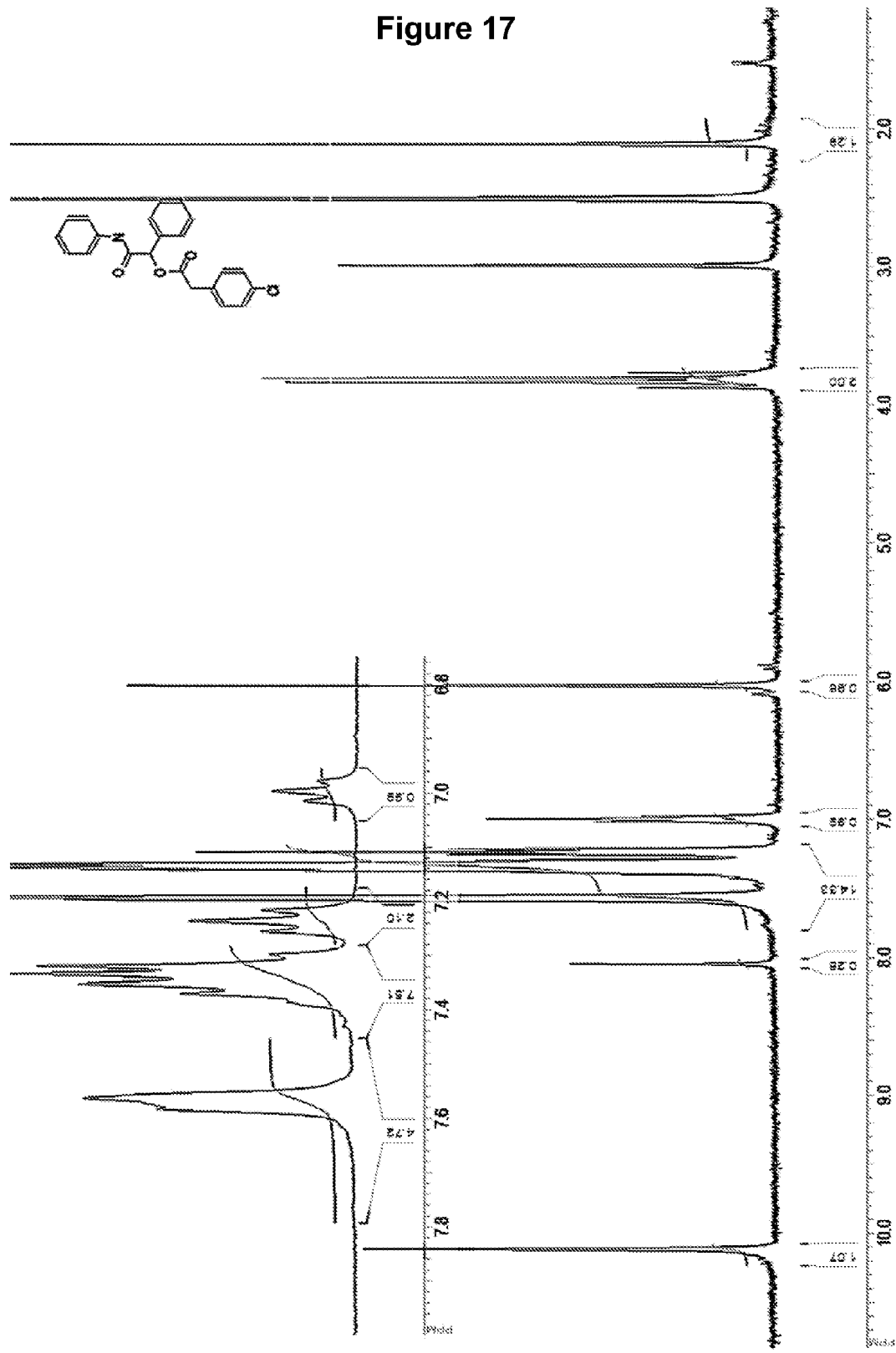
Figure 18:
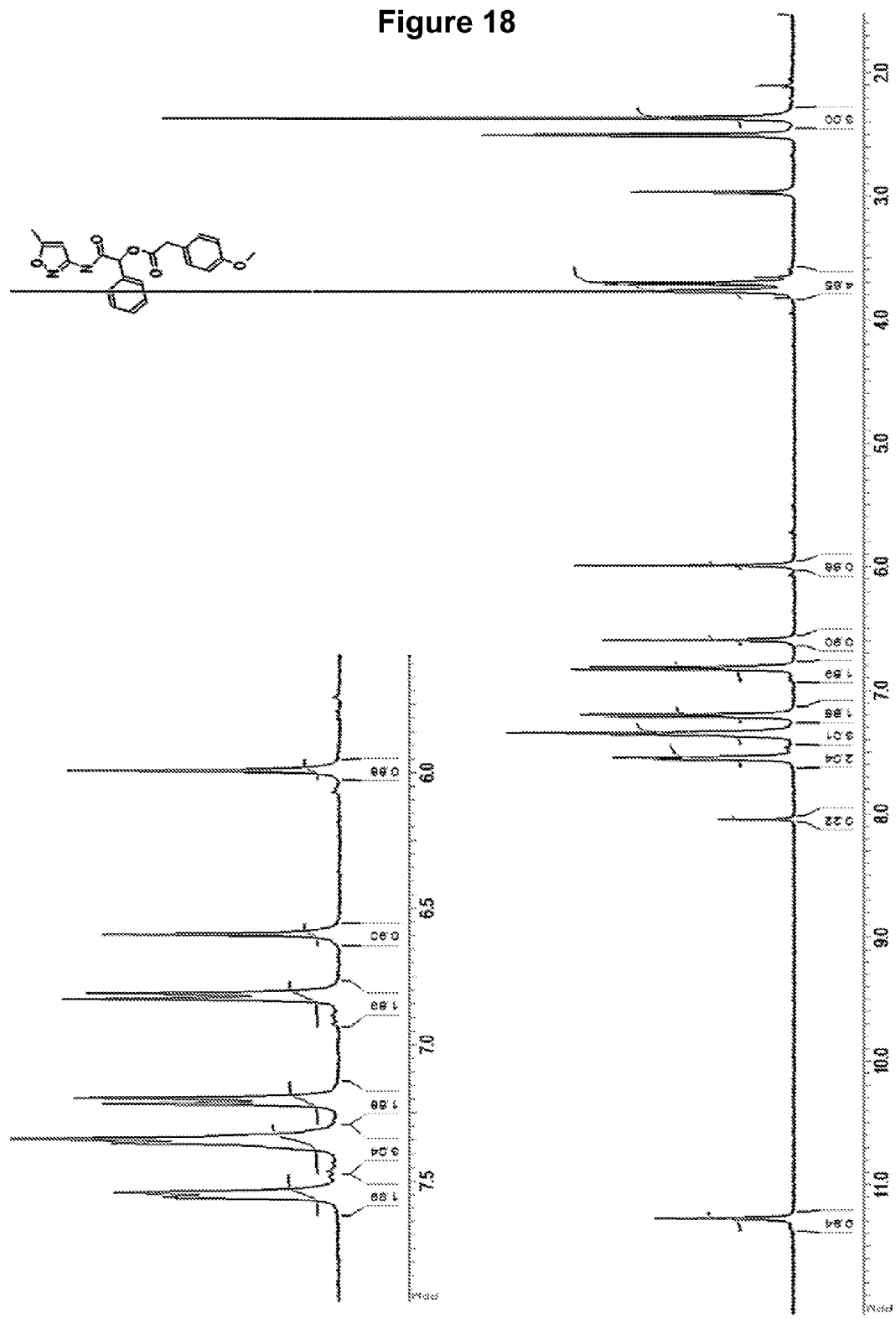
Figure 19:
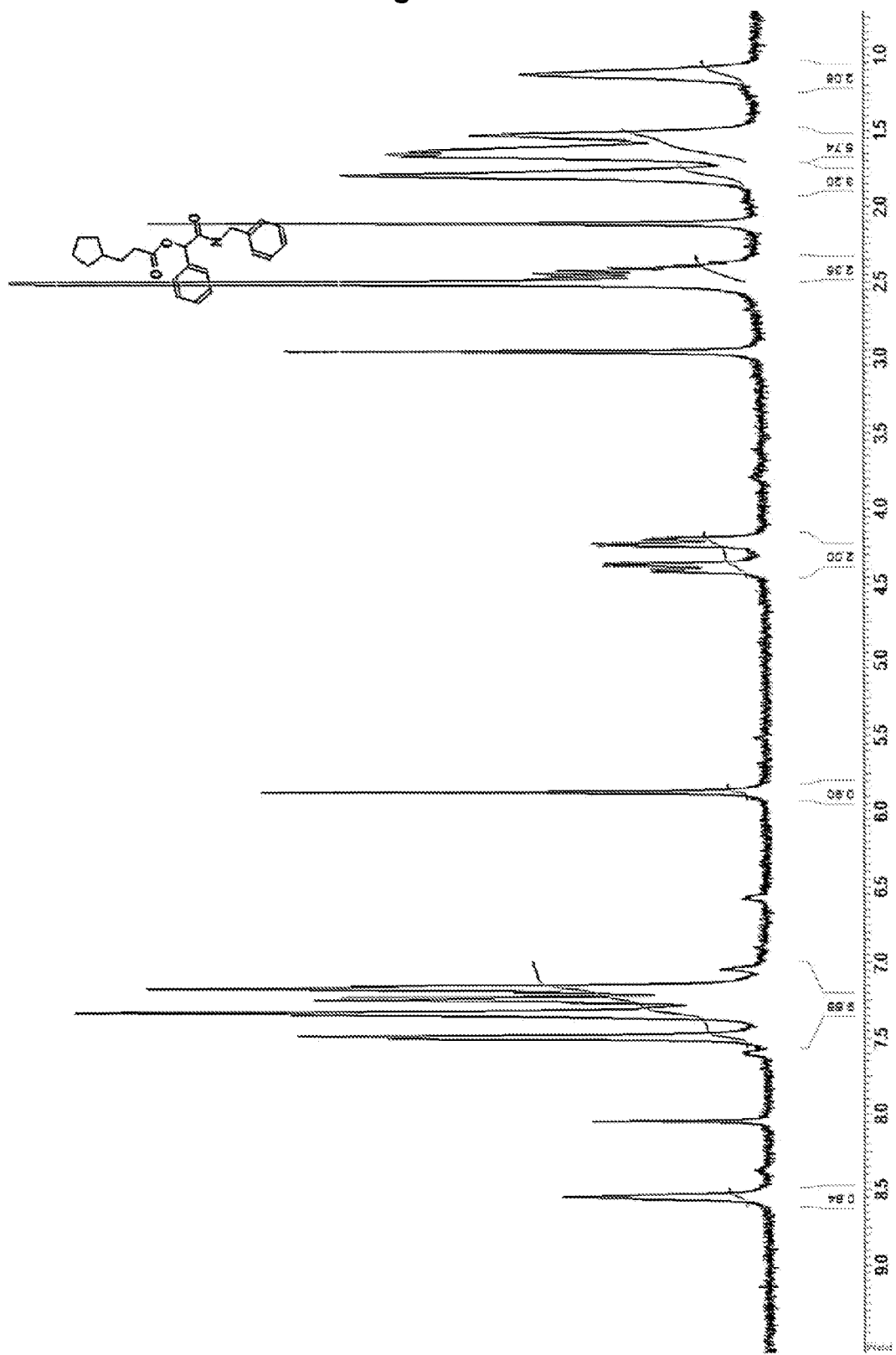
Figure 20:
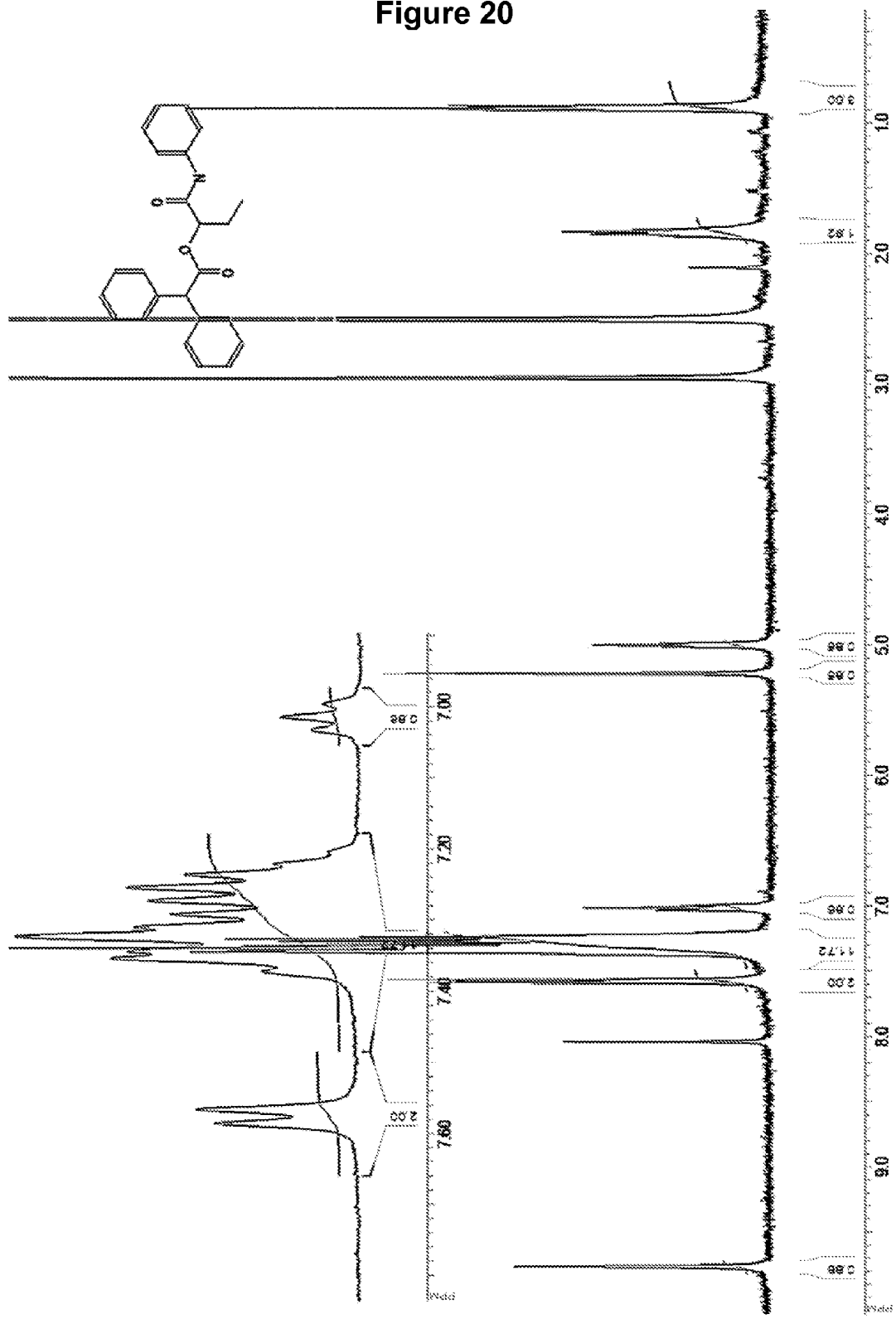
Figure 21:
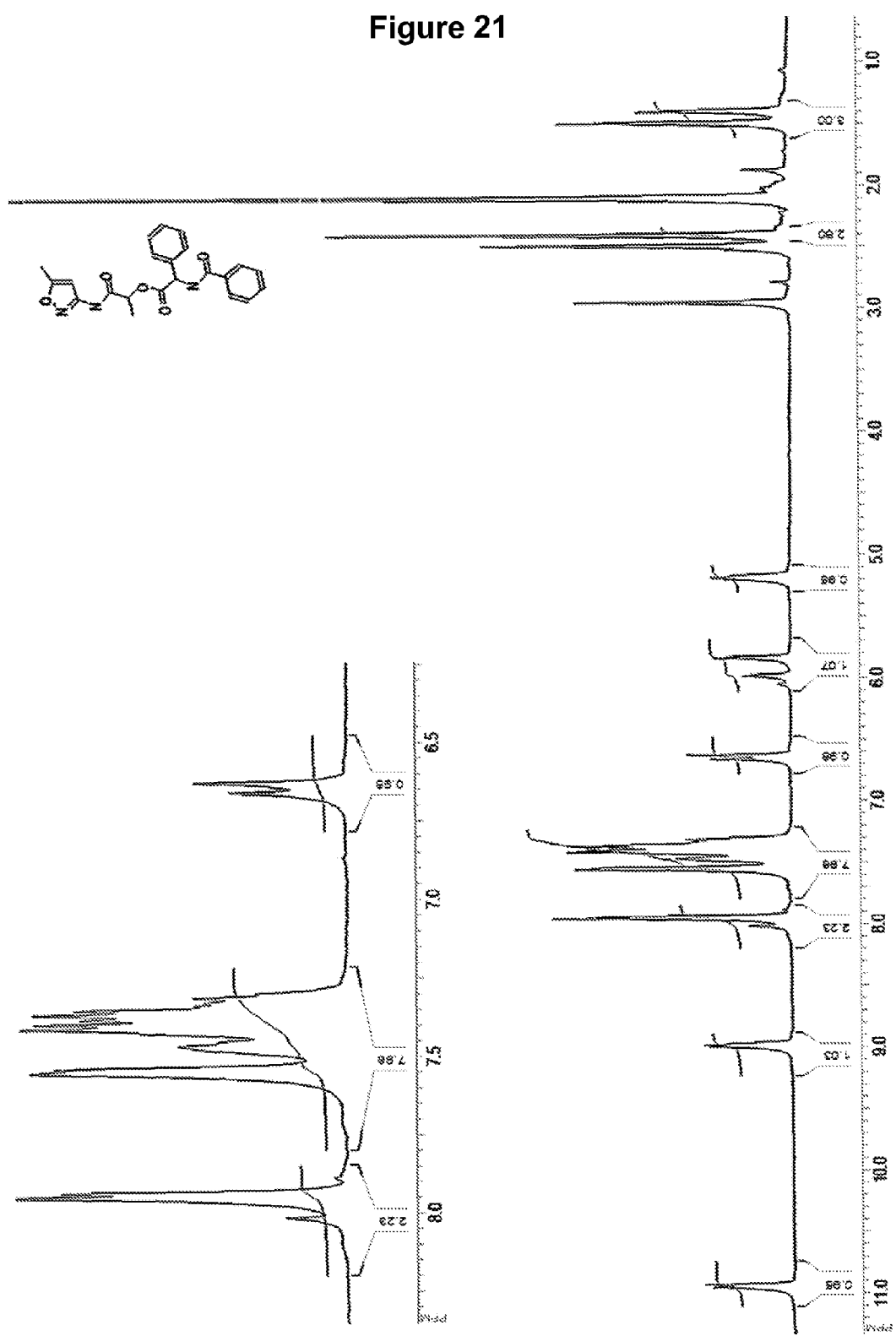
Figure 22:
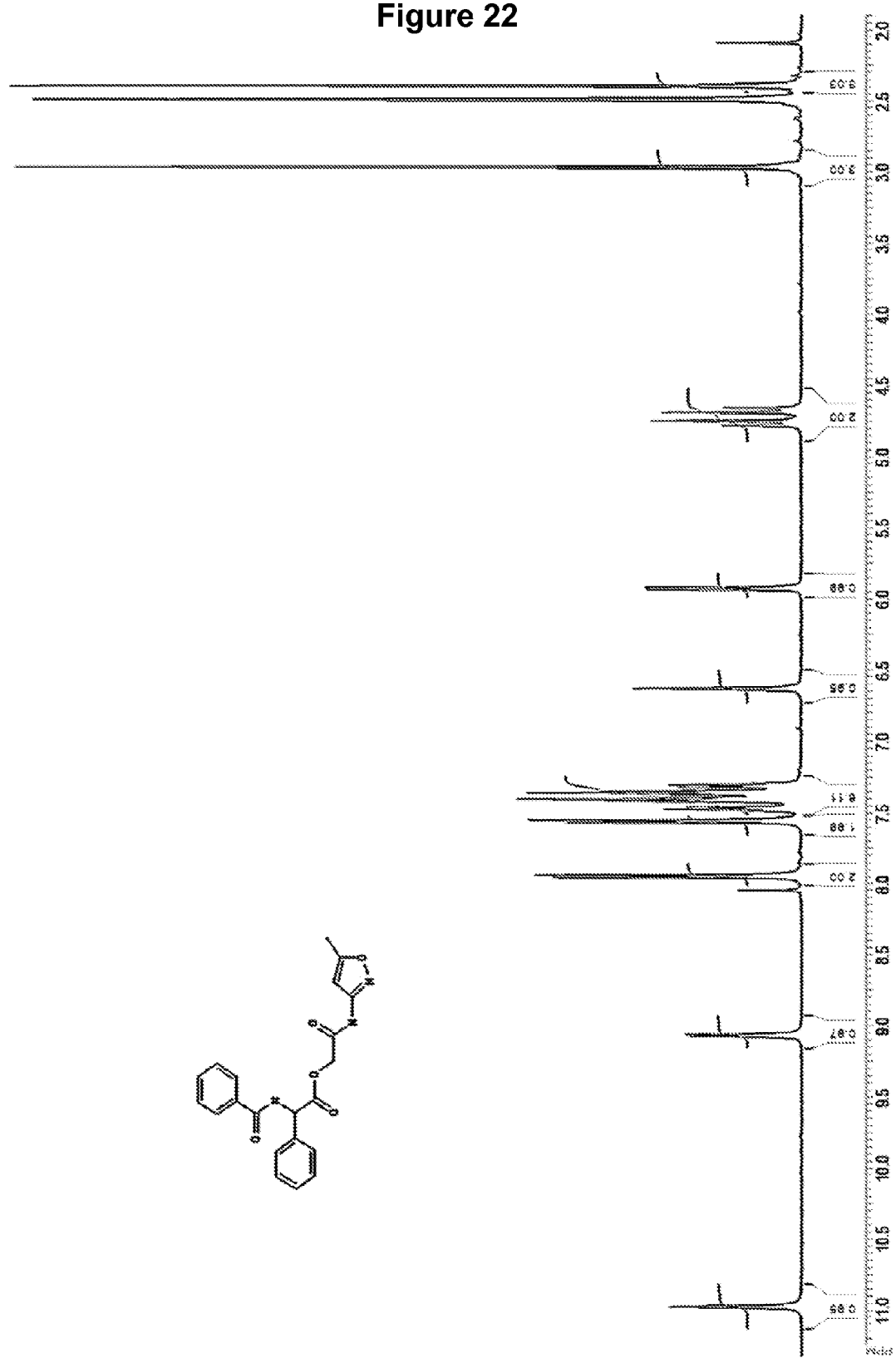

FIG. 1
$^1$H-NMR spectra (400 MHz, DMSO-$d_6$) of compound 4
FIG. 2
$^1$H-NMR spectra 400 MHz, DMSO-$d_6$) of compound 6
FIG. 3
$^1$H-NMR spectra (400 MHz, DMSO-$d_6$) of compound 8
FIG. 4
$^1$H-NMR spectra (500 MHz, DMSO) of compound 9
FIG. 5
$^1$H-NMR spectra (400 MHz, DMSO-$d_6$) of compound 10
FIG. 6
$^1$H-NMR spectra (400 MHz, DMSO-$d_6$+CCl$_4$) of compound 11
FIG. 7
$^1$H-NMR spectra (400 MHz, DMSO-$d_6$) of compound 13
FIG. 8
$^1$H-NMR spectra (400 MHz, DMSO-$d_6$) of compound 14
FIG. 9
$^1$H-NMR spectra (400 MHz, DMSO-$d_6$) of compound 15
FIG. 10
$^1$H-NMR spectra (400 MHz, DMSO-$d_6$) of compound 16
FIG. 11
$^1$H-NMR spectra (400 MHz, DMSO-$d_6$) of compound 19
FIG. 12
$^1$H-NMR spectra (400 MHz, DMSO-$d_6$) of compound 20
FIG. 13
$^1$H-NMR spectra (400 MHz, DMSO-$d_6$+CCl$_4$) of compound 23
FIG. 14
$^1$H-NMR spectra (500 MHz, DMSO) of compound 24
FIG. 15
$^1$H-NMR spectra (400 MHz, DMSO-$d_6$) of compound 25
FIG. 16
$^1$H-NMR spectra (400 MHz, DMSO-$d_6$) of compound 30
FIG. 17
$^1$H-NMR spectra (400 MHz, DMSO-$d_6$) of compound 32
FIG. 18
$^1$H-NMR spectra (400 MHz, DMSO-$d_6$) of compound 36
FIG. 19
$^1$H-NMR spectra (400 MHz, DMSO-$d_6$) of compound 37
FIG. 20
$^1$H-NMR spectra (400 MHz, DMSO-$d_6$) of compound 48
FIG. 21
$^1$H-NMR spectra (500 MHz, DMSO) of compound 52
FIG. 22
$^1$H-NMR spectra (500 MHz, CDCl$_3$) of compound 60

DEFINITIONS

The term "alkyl", as used herein, refers to saturated, straight- or branched-chain hydrocarbon radicals such as "$C_1$-$C_3$ alkyl", "$C_1$-$C_6$ alkyl," or "$C_1$-$C_{12}$ alkyl", containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, isopropyl, n-butyl, tert-butyl, sec-butyl, n-pentyl, neopentyl and n-hexyl radicals; and examples of $C_1$-$C_{12}$ alkyl radicals include, but are not limited to, ethyl, propyl, isopropyl, hexyl, heptyl, octyl, nonyl, decyl, undecyl, dodecyl radicals and the like.

The term "substituted alkyl", as used herein, refers to an alkyl, such as a $C_1$-$C_{12}$ alkyl or $C_1$-$C_6$ alkyl group, substituted by one, two, three or more aliphatic substituents.

Suitable aliphatic substituents include, but are not limited to, —F, —Cl, —Br, —I, —OH, protected hydroxy, aliphatic ethers, aromatic ethers, oxo, —NO$_2$, —CN, —C$_1$-C$_{12}$-alkyl optionally substituted with halogen (such as perhaloalkyls), —C$_2$-C$_{12}$ alkenyl optionally substituted with halogen, —C$_2$-C$_{12}$ alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CO$_2$-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$-heteroaryl, —CO$_2$-heterocycloalkyl, —OCO$_2$—C$_1$-C$_{12}$-alkyl, —OCO$_2$—C$_2$-C$_{12}$-alkenyl, OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C2-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_{2-C12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NR-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NR)NH—C$_1$-C$_{12}$-alkyl, —C(NH)NH—C$_2$-C$_{12}$-alkenyl, —C(NR)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_2$—C-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO2NH-aryl, —SO$_2$NH-heteroaryl —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -hetero arylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$-C$_{12}$-alkenyl" or "C$_2$-C$_6$-alkenyl", as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl", as used herein, refers to a "C$_2$-C$_{12}$-alkenyl" or "C$_2$-C$_6$-alkenyl" group as previously defined, substituted by one, two, three or more aliphatic substituents.

The terms "C$_2$-C$_{12}$-alkynyl" or "C$_2$-C$_6$-alkynyl", as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl", as used herein, refers to a "C$_2$-C$_{12}$-alkynyl" or "C$_2$-C$_6$-alkynyl" group as previously defined, substituted by one, two, three or more aliphatic substituents.

The terms "C$_1$-C$_3$-alkoxy and "C$_1$-C$_6$-alkoxy", as used herein, refers to a C$_1$-C$_3$-alkyl group and C$_1$-C$_6$-alkyl group, as previously defined, attached to the parent molecular moiety through an oxygen atom. Examples of C$_1$-C$_3$-alkoxy include, but are not limited to, methoxy, ethoxy, propoxy. Examples of C$_1$-C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen", as used herein, refer to an atom selected from fluorine, chlorine, bromine and iodine.

The term "aryl", as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl", as used herein, refers to an aryl group, as previously defined, substituted by one, two, three or more aromatic substituents.

Aromatic substituents include, but are not limited to, —F, —Cl, —Br, —I, —OH, protected hydroxy, aliphatic ethers, aromatic ethers, oxo, —NO$_2$, —CN, —C$_1$-C$_{12}$-alkyl optionally substituted with halogen (such as perhaloalkyls), C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH—heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, CONH-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$- heteroaryl, —CO$_2$-heterocycloalkyl, —OCO$_2$—C1-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_2$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —S O$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The term "arylalkyl", as used herein, refers to an aryl group attached to the parent compound via a C$_1$-C$_3$ alkyl or C$_1$-C$_6$ alkyl residue. Examples include, but are not limited to, benzyl, phenethyl and the like.

The term "substituted arylalkyl", as used herein, refers to an arylalkyl group, as previously defined, substituted by one, two, three or more aromatic substituents.

The term "heteroaryl", as used herein, refers to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The term "substituted heteroaryl", as used herein, refers to a heteroaryl group as previously defined, substituted by one, two, three or four aromatic substituents.

The terms "cycloalkyl" or "C$_3$-C$_{12}$-cycloalkyl", as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted C$_3$-C$_{12}$-cycloalkyl," as used herein, refers to a C$_3$-C$_{12}$-cycloalkyl group as previously defined, substituted by one, two, three or more aliphatic substituents.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocycloalkyl", as used herein, refers to a heterocycloalkyl group, as previously defined, substituted by one, two, three or more aliphatic substituents.

The term "heteroarylalkyl", as used herein, to an heteroaryl group attached to the parent compound via a C$_1$-C$_3$ alkyl or C$_1$-C$_6$ alkyl residue. Examples include, but are not limited to, pyridinylmethyl, pyrimidinylethyl and the like.

The term "substituted heteroarylalkyl", as used herein, refers to a heteroarylalkyl group, as previously defined, substituted by independent replacement of one, two, or three or more aromatic substituents.

The term "C$_1$-C$_3$-alkylamino", as used herein, refers to one or two C$_1$-C$_3$-alkyl groups, as previously defined, attached to the parent molecular moiety through a nitrogen atom. Examples of C$_1$-C$_3$-alkylamino include, but are not limited to, methylamino, dimethylamino, ethylamino, diethylamino, and propylamino.

The term "alkylamino" refers to a group having the structure —NH(C$_1$-C$_{12}$-alkyl) where C$_1$-C$_{12}$-alkyl is as previously defined.

The term "dialkylamino" refers to a group having the structure —N(C$_1$-C$_{12}$-alkyl) (C$_1$-C$_{12}$-alkyl), where C$_1$-C$_{12}$-alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde", as used herein, refers to a group of formula —CHO.

The term "carboxy", as used herein, refers to a group of formula —COOH.

The term "carboxamide", as used herein, refers to a group of formula —C(O)NH($C_1$-$C_{12}$-alkyl) or —C(O)N($C_1$-$C_{12}$-alkyl) ($C_1$-$C_{12}$-alkyl), —C(O)$NH_2$, —NHC(O)(C1-$C_{12}$-alkyl), ($C_1$-$C_{12}$-alkyl)C(O)($C_1$-$C_{12}$-alkyl) and the like.

As used herein, the term "pharmaceutically acceptable salts" includes acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion using a suitable ion exchange resin.

In the context of the present specification, the term "treat" also includes "prophylaxis" unless there are specific indications to the contrary. The term "treat" within the context of the present invention further encompasses to administer an effective amount of a compound of the present invention, to mitigate either a pre-existing disease state, acute or chronic, or a recurring condition. This definition also encompasses prophylactic therapies for prevention of recurring condition and continued therapy for chronic disorders.

The compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the present invention, the route of administration may be topical.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of the present invention, inert, pharmaceutically acceptable carriers can be either solid or liquid. Solid form preparations include powders, tablets, dispersable granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

In powders, the carrier is a finely divided solid, which is in mixture with the finely divided compound of the present invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogenous mixture is then poured into conveniently sized molds and allowed to cool and solidify.

Suitable carriers are magnesium carbonate, magnesium stearate, talc, lactose, sugar, pectin, dextrin, starch, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

The above-mentioned subject-matter for a pharmaceutical composition comprising a compound according to the present invention is applied analogously for a pharmaceutical composition comprising a combination according to the present invention.

Another object of the present invention is a compound as disclosed above for use in medicine.

Another object of the present invention is a pharmaceutical formulation comprising a compound as disclosed above in admixture with pharmaceutically acceptable adjuvants, diluents and/or carriers.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

EXAMPLES

KLK7 Inhibitor Test

Substrate:(MeO-Suc-Arg-Pro-Tyr-pNA), acetate salt, Peptide international, lot #906841, previously named S-2586

Enzyme: Active human KLK7 (SCCE) 0.62 mg/ml in 0.3 M NaCl, 10 mM NaAc, pH 4

Buffer: 10 mM NaPhospate, 0.5 M NaCl, pH 7.2

150 µl of Substrate (2.5 mM) in Buffer was added to 96 wells plate (F8 Polysorp Unfra, Nunc cat. no. 469957). 10 µl of DMSO was added to the blank and control wells.

10 µl of substance in DMSO was added to wells giving final concentrations of 20 µM, 10 µM, 5 µM, 2.5 µM, 1.25 µM, 0.625 µM, 0.3125 µM, and 0.15625 µM.

40 µl of active KLK7 (SCCE) (diluted to 12.5 µg/ml in activity buffer) was added all wells except blank to which activity buffer was added.

Immediately after addition of SCCE the plate was transferred to a Spectramax 250 Microplate Reader (Molecular Devices) and enzyme activity (V) was measured as release of pNa measuring absorbance at 405 nm in 37° C. for 15 min with reading every 30 s.

The mean value V of each sample was calculated (n=2 for the substances and n=4 for the control). From the values of V the % of total activity was calculated as $(V_{inhibitor}/V_{control}$ (no inhibitor))×100.

Plotting and calculation was then done in originPro.

% of total activity (y) was plotted vs. log [inhibitor] (log x) and a function of dose response $$y = A1 + (A2 - A1)/(1 + 10^{((LOG(x0)-x)*p)})$$

where A1=Bottom platue, A2=Top platue, $x0 = EC_{50}$ and p=Hill slope was fitted to the curve. $IC_{50}$ concentration was calculated by setting y=50 and solving for x.

The $IC_{50}$ values were used to identify KLK7 inhibitors according to the invention.

Results are presented in Table 1.

$IC_{50}$ values of compounds according to Formula I

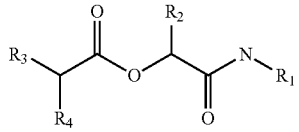

Formula I wherein $R_1$, $R_2$, $R_3$ and $R_4$ are as defined in Table 1 below.

TABLE 1

| Cmpd | Structure | $R_1$ | $R_2$ | $R_3$ | $R_4$ | IC50 (µm) |
|---|---|---|---|---|---|---|
| 1 | 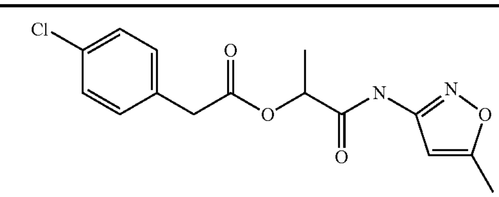 | 5-methyl-3-isoxazolyl- | -methyl | 4-chloro-phenyl- | —H | 0.039 |
| 2 | 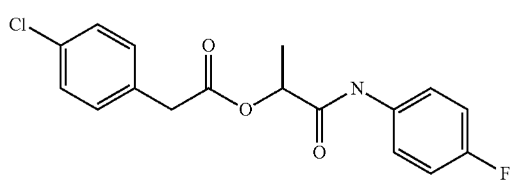 [SMILES: CC(OC(=O)Cc1ccc(Cl)cc1)C(=O)Nc1ccc(F)cc1] | 4-fluoro-phenyl- | -methyl | 4-chloro-phenyl- | —H | 0.07 |
| 3 | 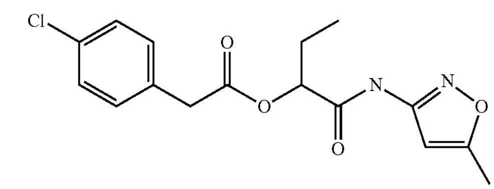 [SMILES: CCC(OC(=O)Cc1ccc(Cl)cc1)C(=O)Nc1cc(C)on1] | 5-methyl-3-isoxazolyl- | -ethyl | 4-chloro-phenyl- | —H | 0.08 |
| 4 | 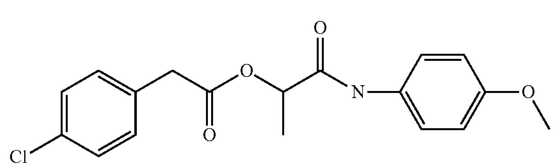 [SMILES: COc1ccc(NC(=O)C(C)OC(=O)Cc2ccc(Cl)cc2)cc1] | 4-methoxy-phenyl- | -methyl | 4-chloro-phenyl- | —H | 0.08 |
| 5 | 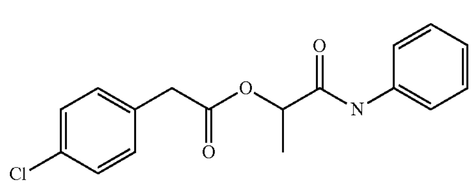 [SMILES: CC(OC(=O)Cc1ccc(Cl)cc1)C(=O)Nc1ccccc1] | -phenyl | -methyl | 4-chloro-phenyl- | —H | 0.09 |

TABLE 1-continued

| Cmpd | Structure | R₁ | R₂ | R₃ | R₄ | IC50 (μm) |
|---|---|---|---|---|---|---|
| 6 | 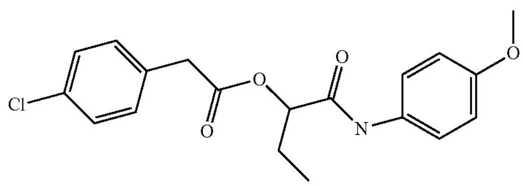 [SMILES: CCC(OC(=O)Cc1ccc(Cl)cc1)C(=O)Nc1ccc(OC)cc1] | 4-methoxy-phenyl- | -ethyl | 4-chloro-phenyl- | —H | 0.12 |
| 7 | 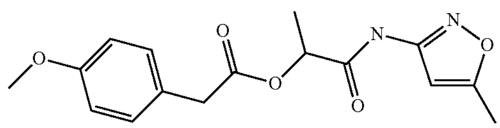 | 5-methyl-3-isoxazolyl- | -methyl | 4-methoxy-phenyl | —H | 0.13 |
| 8 | 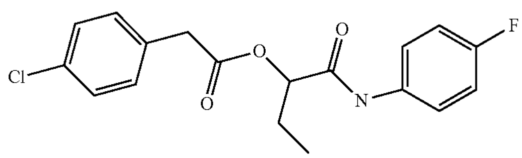 [SMILES: CCC(OC(=O)Cc1ccc(Cl)cc1)C(=O)Nc1ccc(F)cc1] | 4-fluoro-phenyl- | -ethyl | 4-chloro-phenyl- | —H | 0.14 |
| 9 | 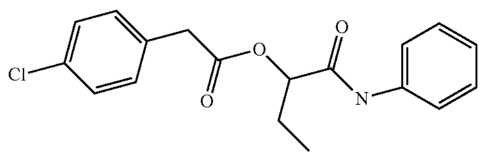 [SMILES: CCC(OC(=O)Cc1ccc(Cl)cc1)C(=O)Nc1ccccc1] | -phenyl | -ethyl | 4-chloro-phenyl- | —H | 0.15 |
| 10 | 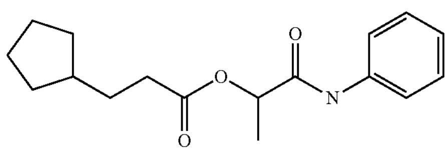 [SMILES: CC(OC(=O)CCC1CCCC1)C(=O)Nc1ccccc1] | 4-methoxy-phenyl- | -methyl | cyclopentyl methyl- | —H | 0.15 |
| 11 | 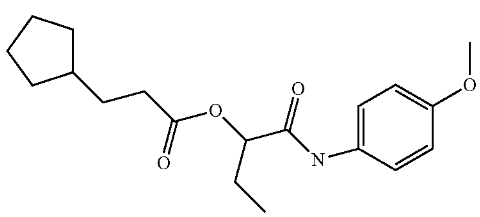 [SMILES: CCC(OC(=O)CCC1CCCC1)C(=O)Nc1ccc(OC)cc1] | 4-methoxy-phenyl- | -ethyl | cyclopentyl methyl- | —H | 0.15 |
| 12 | 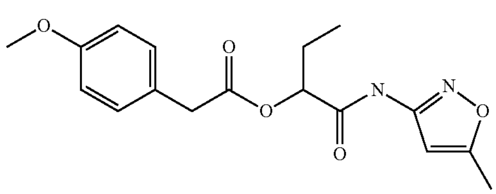 | 5-methyl-3-isoxazolyl- | -ethyl | 4-methoxy-phenyl | —H | 0.15 |
| 13 | 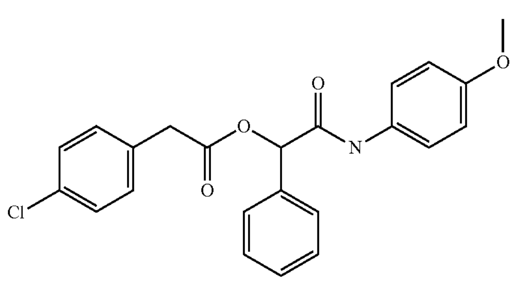 [SMILES: COc1ccc(NC(=O)C(OC(=O)Cc2ccc(Cl)cc2)c2ccccc2)cc1] | 4-methoxy-phenyl- | -phenyl | 4-chloro-phenyl- | —H | 0.17 |

TABLE 1-continued

| Cmpd | Structure | R₁ | R₂ | R₃ | R₄ | IC50 (μm) |
|---|---|---|---|---|---|---|
| 14 | 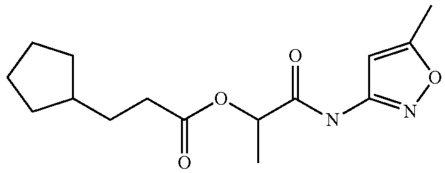 [SMILES: Cc1cc(NC(=O)C(C)OC(=O)CCC2CCCC2)no1] | 5-methyl-3-isoxazolyl- | -methyl | cyclopentyl methyl- | —H | 0.18 |
| 15 | 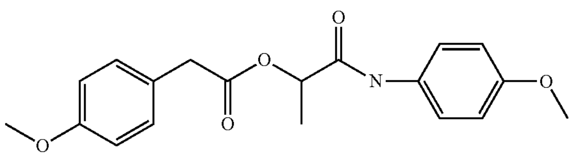 | 4-methoxy-phenyl- | -methyl | 4-methoxy-phenyl | —H | 0.18 |
| 16 | 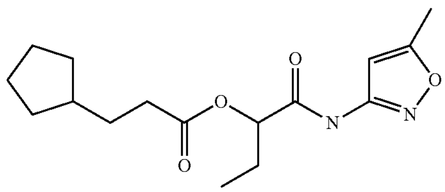 [SMILES: CCC(OC(=O)CCC1CCCC1)C(=O)Nc1cc(C)on1] | 5-methyl-3-isoxazolyl- | methyl- | cyclopentyl methyl- | —H | 0.19 |
| 17 | 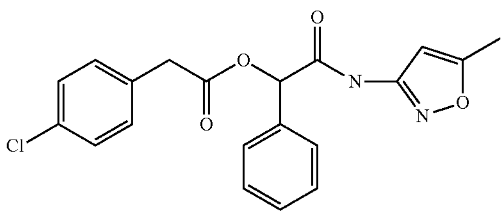 [SMILES: Cc1cc(NC(=O)C(OC(=O)Cc2ccc(Cl)cc2)c2ccccc2)no1] | 5-methyl-3-isoxazolyl- | -phenyl | 4-chloro-phenyl- | —H | 0.19 |
| 18 | 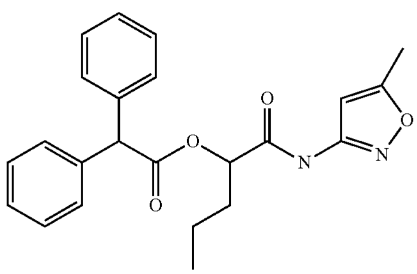 [SMILES: CCCC(OC(=O)C(c1ccccc1)c1ccccc1)C(=O)Nc1cc(C)on1] | 5-methyl-3-isoxazolyl- | -propyl | -phenyl | -phenyl | 0.22 |
| 19 | 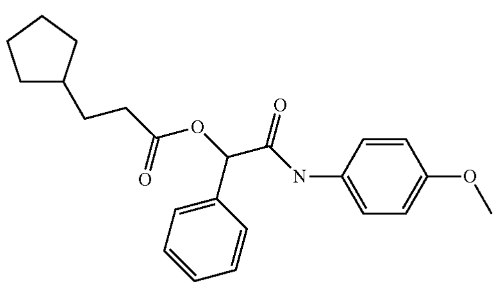 [SMILES: COc1ccc(NC(=O)C(OC(=O)CCC2CCCC2)c2ccccc2)cc1] | 4-methoxy-phenyl- | -phenyl | cyclopentyl methyl- | —H | 0.23 |
| 20 | 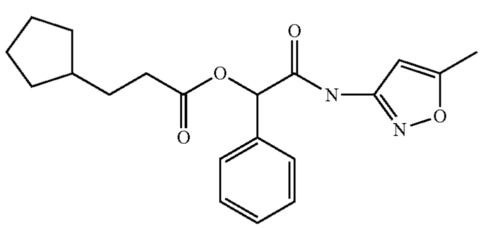 [SMILES: Cc1cc(NC(=O)C(OC(=O)CCC2CCCC2)c2ccccc2)no1] | 5-methyl-3-isoxazolyl- | -phenyl | cyclopentyl methyl- | —H | 0.23 |

TABLE 1-continued

| Cmpd | Structure | R₁ | R₂ | R₃ | R₄ | IC50 (µm) |
|---|---|---|---|---|---|---|
| 21 | 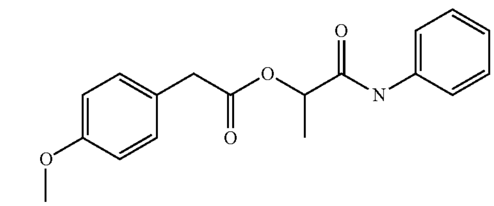 [SMILES: COc1ccc(CC(=O)OC(C)C(=O)Nc2ccccc2)cc1] | -phenyl | -methyl | 4-methoxy-phenyl | —H | 0.26 |
| 22 | 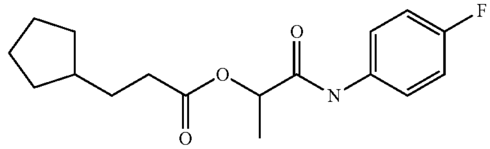 [SMILES: CC(OC(=O)CCC1CCCC1)C(=O)Nc1ccc(F)cc1] | 4-fluoro-phenyl- | -methyl | cyclopentyl methyl- | —H | 0.26 |
| 23 | 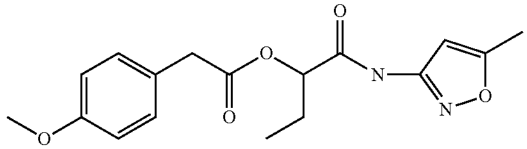 | 5-methyl-3-isoxazolyl- | -ethyl | 4-methoxy-phenyl | —H | 0.27 |
| 24 | 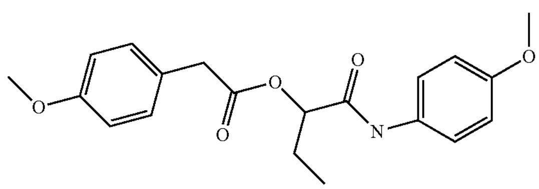 | 4-methoxy-phenyl- | -ethyl | 4-methoxy-phenyl | —H | 0.28 |
| 25 | 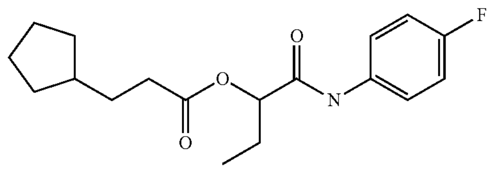 [SMILES: CCC(OC(=O)CCC1CCCC1)C(=O)Nc1ccc(F)cc1] | 4-fluoro-phenyl- | -ethyl | cyclopentyl methyl- | —H | 0.31 |
| 26 | 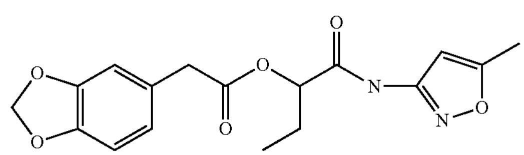 [SMILES: CCC(OC(=O)Cc1ccc2c(c1)OCO2)C(=O)Nc1cc(C)on1] | 5-methyl-3-isoxazolyl- | -ethyl | 1,3-benzo-dioxolyl- | —H | 0.32 |
| 27 | 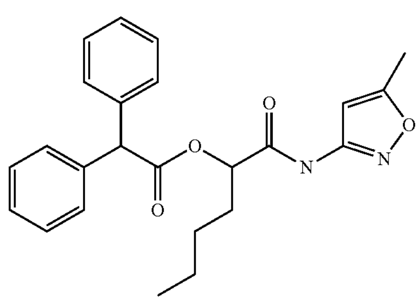 [SMILES: CCCCC(OC(=O)C(c1ccccc1)c1ccccc1)C(=O)Nc1cc(C)on1] | 5-methyl-3-isoxazolyl- | -butyl | -phenyl | -phenyl | 0.33 |
| 28 | 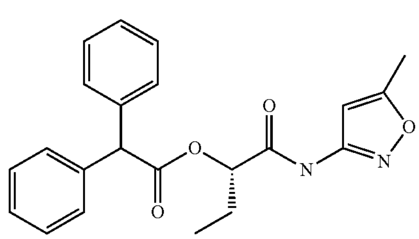 [SMILES: CC[C@H](OC(=O)C(c1ccccc1)c1ccccc1)C(=O)Nc1cc(C)on1] | 5-methyl-3-isoxazolyl- | -ethyl | -phenyl | -phenyl | 0.34 |

TABLE 1-continued

| Cmpd | Structure | R₁ | R₂ | R₃ | R₄ | IC50 (μm) |
|------|-----------|-----|-----|-----|-----|-----------|
| 29 | 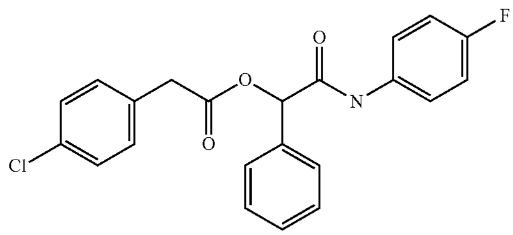 [SMILES: O=C(Cc1ccc(Cl)cc1)OC(C(=O)Nc1ccc(F)cc1)c1ccccc1] | 4-fluoro-phenyl- | -phenyl | 4-chloro-phenyl- | —H | 0.35 |
| 30 | 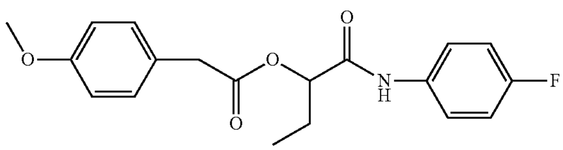 [SMILES: CCC(OC(=O)Cc1ccc(OC)cc1)C(=O)Nc1ccc(F)cc1] | 4-fluoro-phenyl- | -ethyl | 4-methoxy-phenyl- | —H | 0.36 |
| 31 | 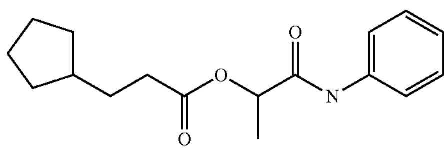 [SMILES: CC(OC(=O)CCC1CCCC1)C(=O)Nc1ccccc1] | -phenyl | -methyl | cyclopentyl methyl- | —H | 0.37 |
| 32 | 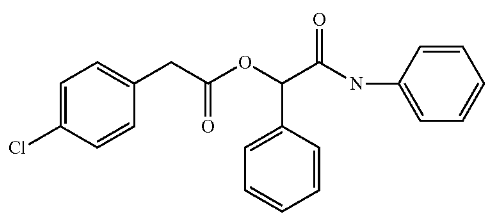 [SMILES: O=C(Cc1ccc(Cl)cc1)OC(C(=O)Nc1ccccc1)c1ccccc1] | -phenyl | -phenyl | 4-chloro-phenyl- | —H | 0.38 |
| 33 | 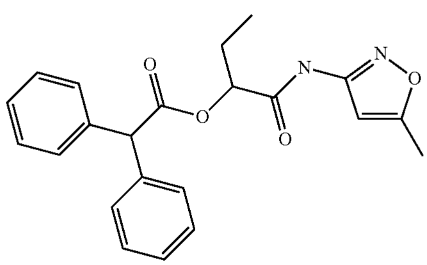 [SMILES: CCC(OC(=O)C(c1ccccc1)c1ccccc1)C(=O)Nc1cc(C)on1] | 5-methyl-3-isoxazolyl- | -ethyl | -phenyl | -phenyl | 0.39 |
| 34 | 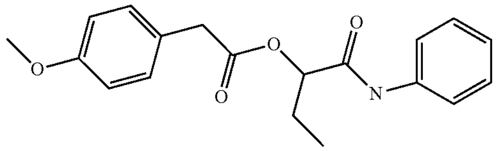 [SMILES: CCC(OC(=O)Cc1ccc(OC)cc1)C(=O)Nc1ccccc1] | -phenyl | -ethyl | 4-methoxy-phenyl- | —H | 0.39 |
| 35 | 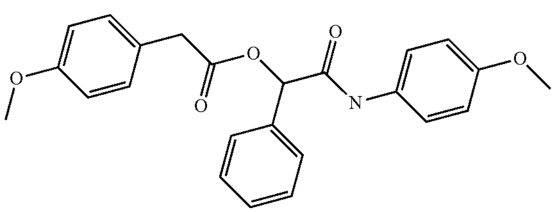 | 4-methoxy-phenyl- | -phenyl | 4-methoxy-phenyl- | —H | 0.41 |

TABLE 1-continued

| Cmpd | Structure | R₁ | R₂ | R₃ | R₄ | IC50 (μm) |
|---|---|---|---|---|---|---|
| 36 | 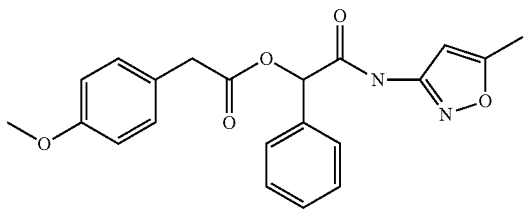 | 5-methyl-3-isoxazolyl- | -phenyl | 4-methoxy-phenyl- | —H | 0.43 |
| 37 | 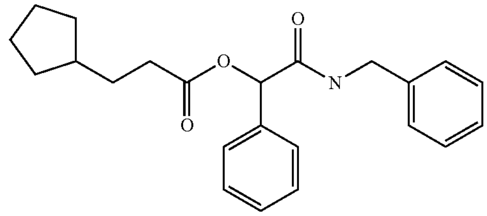 [SMILES: O=C(CCC1CCCC1)OC(C(=O)NCc1ccccc1)c1ccccc1] | -phenyl | -phenyl | cyclopentyl methyl- | —H | 0.46 |
| 38 | 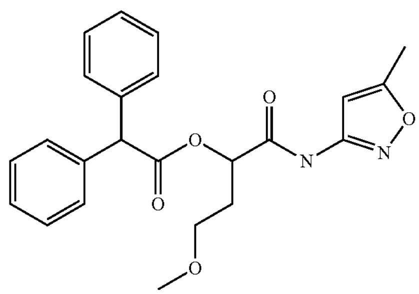 [SMILES: COCCC(OC(=O)C(c1ccccc1)c1ccccc1)C(=O)Nc1cc(C)on1] | 5-methyl-3-isoxazolyl- | methoxy-propyl- | -phenyl | -phenyl | 0.47 |
| 39 | 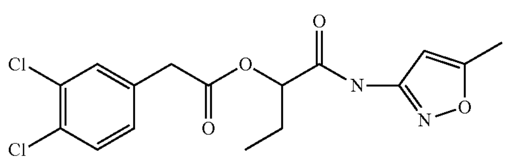 [SMILES: CCC(OC(=O)Cc1ccc(Cl)c(Cl)c1)C(=O)Nc1cc(C)on1] | 5-methyl-3-isoxazolyl- | -ethyl | 3,4-dichloro-phenyl- | —H | 0.48 |
| 40 | 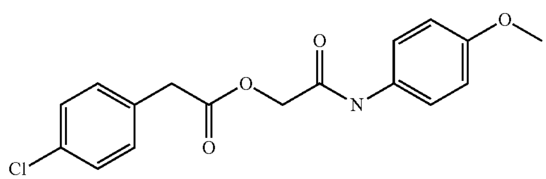 | 4-methoxy-phenyl- | —H | 4-chloro-phenyl- | —H | 0.55 |
| 41 | 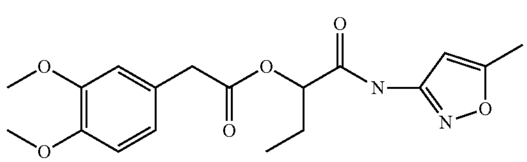 | 5-methyl-3-isoxazolyl- | -ethyl | 3,4-dimethoxy-phenyl- | —H | 0.58 |
| 42 | 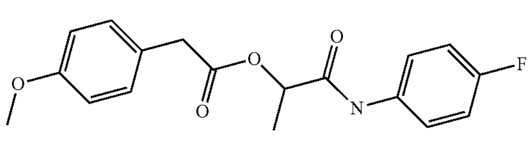 [SMILES: COc1ccc(CC(=O)OC(C)C(=O)Nc2ccc(F)cc2)cc1] | 4-fluoro-phenyl- | -methyl | 4-methoxy-phenyl- | —H | 0.59 |

TABLE 1-continued

| Cmpd | Structure | R₁ | R₂ | R₃ | R₄ | IC50 (μm) |
|---|---|---|---|---|---|---|
| 43 | 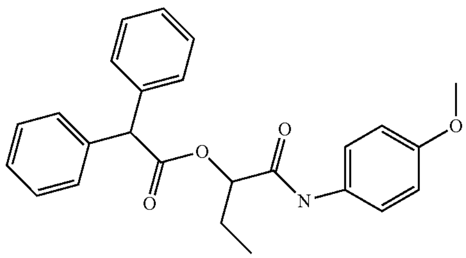 [SMILES: CCC(OC(=O)C(c1ccccc1)c1ccccc1)C(=O)Nc1ccc(OC)cc1] | 4-methoxy-phenyl- | -ethyl | -phenyl | -phenyl | 0.63 |
| 44 | 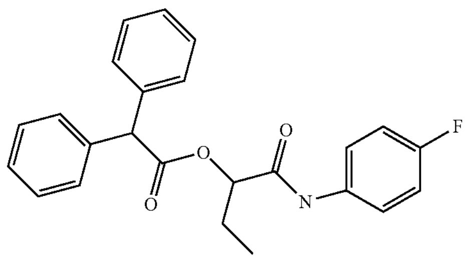 | 4-fluoro-phenyl- | -ethyl | -phenyl | -phenyl | 0.64 |
| 45 | 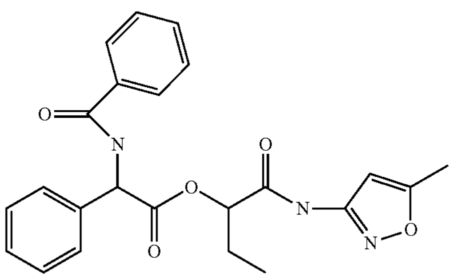 [SMILES: CCC(OC(=O)C(NC(=O)c1ccccc1)c1ccccc1)C(=O)Nc1cc(C)on1] | 5-methyl-3-isoxazolyl- | -ethyl | benzamido | -phenyl | 0.66 |
| 46 | 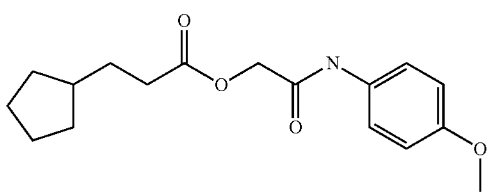 | 4-methoxy-phenyl- | —H | cyclopentyl methyl- | —H | 0.69 |
| 47 | 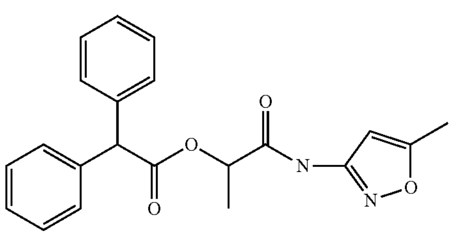 [SMILES: Cc1cc(NC(=O)C(C)OC(=O)C(c2ccccc2)c2ccccc2)no1] | 5-methyl-3-isoxazolyl- | -methyl | -phenyl | -phenyl | 0.74 |
| 48 | 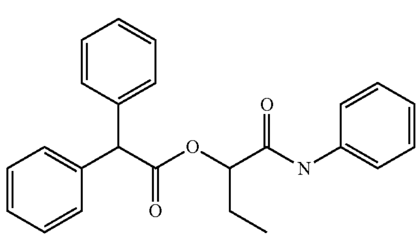 [SMILES: CCC(OC(=O)C(c1ccccc1)c1ccccc1)C(=O)Nc1ccccc1] | -phenyl | -ethyl | -phenyl | -phenyl | 0.76 |

TABLE 1-continued
| Cmpd | Structure | R₁ | R₂ | R₃ | R₄ | IC50 (μm) |
|---|---|---|---|---|---|---|
| 49 | 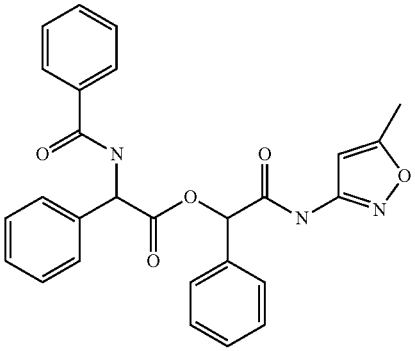 [SMILES: Cc1cc(NC(=O)C(OC(=O)C(NC(=O)c2ccccc2)c2ccccc2)c2ccccc2)no1] | 5-methyl-3-isoxazolyl- | -phenyl | benzamido | -phenyl | 0.78 |
| 50 | 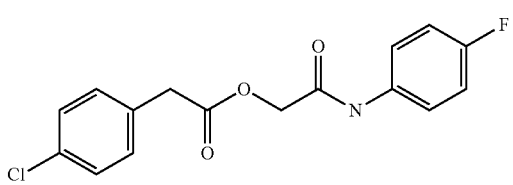 | 4-fluorophenyl- | —H | 4-chlorophenyl- | —H | 0.79 |
| 51 | 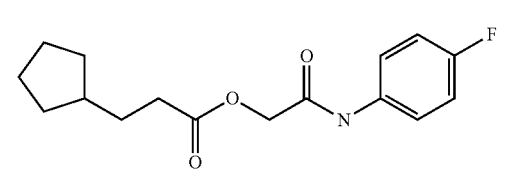 | 4-fluorophenyl- | —H | cyclopentylmethyl- | —H | 0.83 |
| 52 | 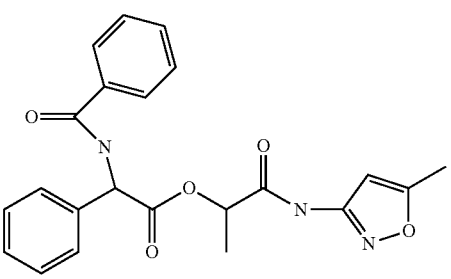 [SMILES: Cc1cc(NC(=O)C(C)OC(=O)C(NC(=O)c2ccccc2)c2ccccc2)no1] | 5-methyl-3-isoxazolyl- | -methyl | -benzamido | -phenyl | 0.95 |
| 53 | 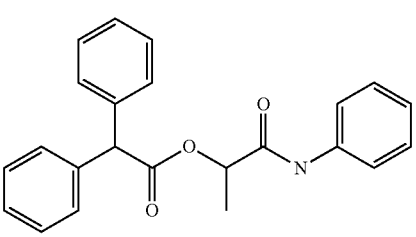 [SMILES: CC(OC(=O)C(c1ccccc1)c1ccccc1)C(=O)Nc1ccccc1] | -phenyl | -methyl | -phenyl | -phenyl | 1.10 |
| 54 | 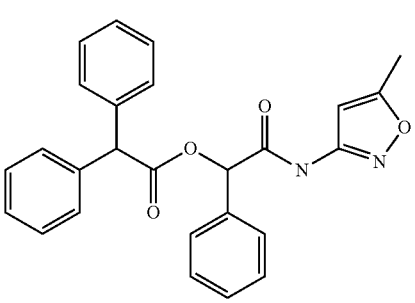 [SMILES: Cc1cc(NC(=O)C(OC(=O)C(c2ccccc2)c2ccccc2)c2ccccc2)no1] | 5-methyl-3-isoxazolyl- | -phenyl | -phenyl | -phenyl | 1.1 |

TABLE 1-continued
| Cmpd | Structure | $R_1$ | $R_2$ | $R_3$ | $R_4$ | IC50 (μm) |
|---|---|---|---|---|---|---|
| 55 | 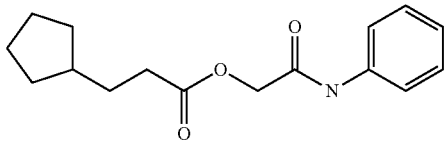 | -phenyl | —H | cyclopentylmethyl- | —H | 1.11 |
| 56 | 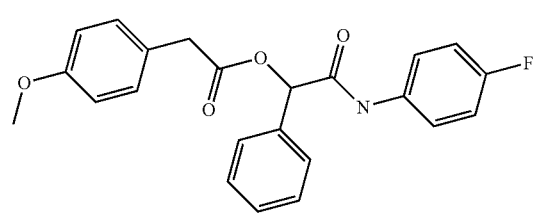 [SMILES: COc1ccc(CC(=O)OC(C(=O)Nc2ccc(F)cc2)c2ccccc2)cc1] | 4-fluorophenyl- | -phenyl | 4-methoxyphenyl- | —H | 1.17 |
| 57 | 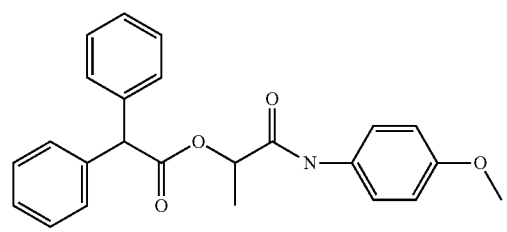 [SMILES: COc1ccc(NC(=O)C(C)OC(=O)C(c2ccccc2)c2ccccc2)cc1] | 4-methoxyphenyl- | -methyl | -phenyl | -phenyl | 1.18 |
| 58 | 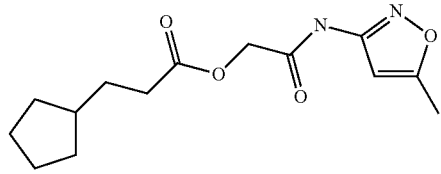 | 5-methyl-3-isoxazolyl- | —H | cyclopentylmethyl- | —H | 1.20 |
| 59 | 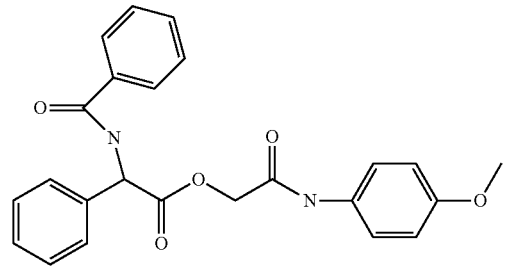 [SMILES: COc1ccc(NC(=O)COC(=O)C(NC(=O)c2ccccc2)c2ccccc2)cc1] | 4-methoxyphenyl- | —H | -benzamido | -phenyl | 1.23 |
| 60 | 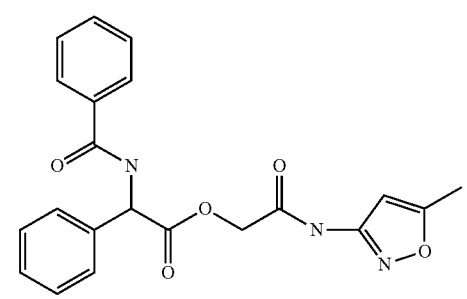 [SMILES: Cc1cc(NC(=O)COC(=O)C(NC(=O)c2ccccc2)c2ccccc2)no1] | 5-methyl-3-isoxazolyl- | —H | -benzamido | -phenyl | 1.47 |

TABLE 1-continued

| Cmpd | Structure | R₁ | R₂ | R₃ | R₄ | IC50 (μm) |
|---|---|---|---|---|---|---|
| 61 | 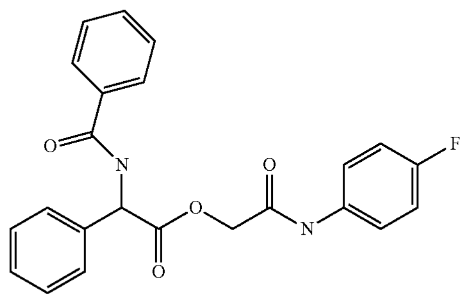 [SMILES: O=C(COC(=O)C(NC(=O)c1ccccc1)c1ccccc1)Nc1ccc(F)cc1] | 4-fluoro-phenyl- | —H | -benzamido | -phenyl | 1.51 |
| 62 | 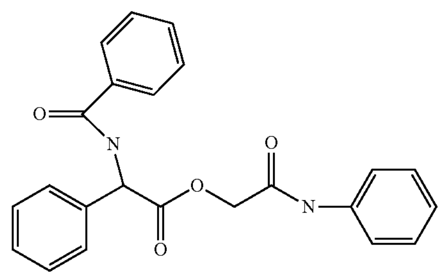 [SMILES: O=C(COC(=O)C(NC(=O)c1ccccc1)c1ccccc1)Nc1ccccc1] | -phenyl | —H | -benzamido | -phenyl | 1.56 |
| 63 | 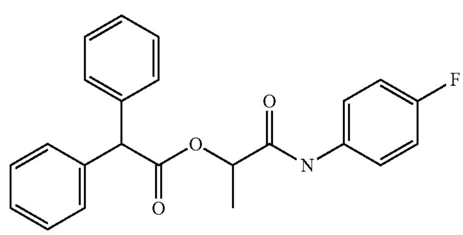 [SMILES: CC(OC(=O)C(c1ccccc1)c1ccccc1)C(=O)Nc1ccc(F)cc1] | 4-fluoro-phenyl- | -methyl | -phenyl | -phenyl | 1.62 |
| 64 | 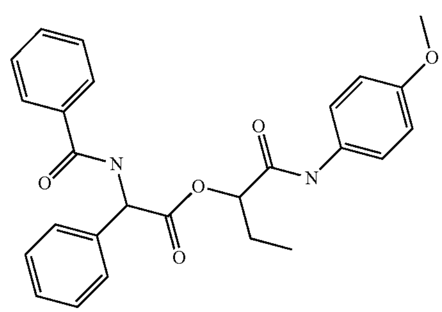 [SMILES: CCC(OC(=O)C(NC(=O)c1ccccc1)c1ccccc1)C(=O)Nc1ccc(OC)cc1] | 4-methoxy-phenyl- | -ethyl | -benzamido | -phenyl | 1.7 |
| 65 | 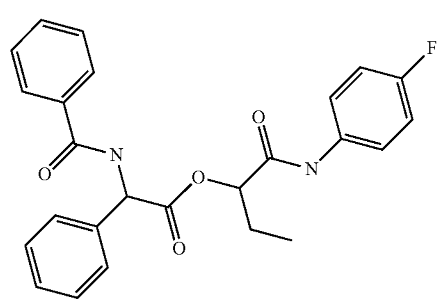 [SMILES: CCC(OC(=O)C(NC(=O)c1ccccc1)c1ccccc1)C(=O)Nc1ccc(F)cc1] | 4-fluoro-phenyl- | -ethyl | -benzamido | -phenyl | 1.79 |

TABLE 1-continued

| Cmpd | Structure | R₁ | R₂ | R₃ | R₄ | IC50 (μm) |
|---|---|---|---|---|---|---|
| 66 | 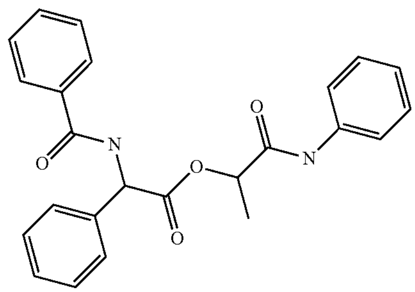 [SMILES: CC(OC(=O)C(NC(=O)c1ccccc1)c1ccccc1)C(=O)Nc1ccccc1] | -phenyl | -methyl | -benzamido | -phenyl | 1.85 |
| 67 | 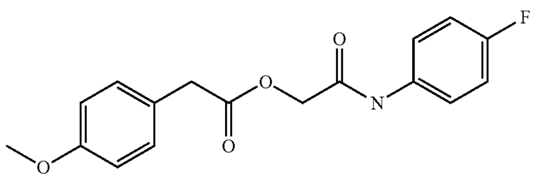 | 4-fluoro-phenyl- | —H | 4-methoxy-phenyl- | —H | 2.28 |
| 68 | 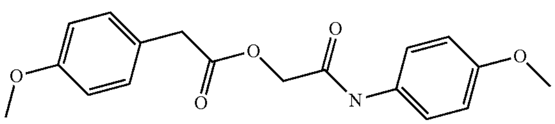 | 4-methoxy-phenyl- | —H | 4-methoxy-phenyl- | —H | 2.31 |
| 69 | 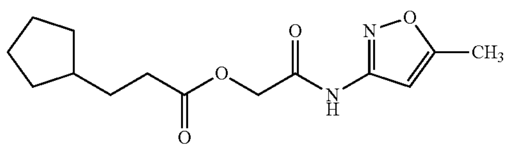 | 5-methyl-3-isoxazolyl- | —H | cyclopentyl methyl- | —H | 2.7 |
| 70 | 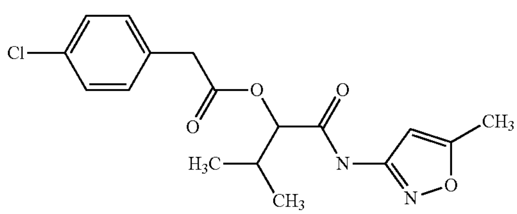 [SMILES: Cc1cc(NC(=O)C(OC(=O)Cc2ccc(Cl)cc2)C(C)C)no1] | 5-methyl-3-isoxazolyl- | -isopropyl | 4-chloro-phenyl- | —H | 2.7 |
| 71 | 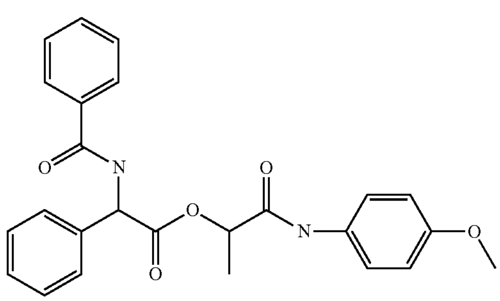 [SMILES: COc1ccc(NC(=O)C(C)OC(=O)C(NC(=O)c2ccccc2)c2ccccc2)cc1] | 4-methoxy-phenyl- | -methyl | -benzamido | -phenyl | 2.76 |
| 72 | 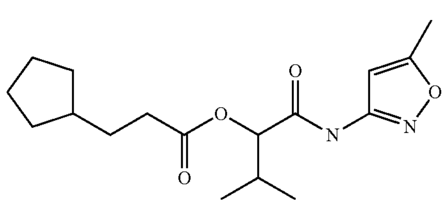 [SMILES: Cc1cc(NC(=O)C(OC(=O)CCC2CCCC2)C(C)C)no1] | 5-methyl-3-isoxazolyl- | -isopropyl | cyclopentyl methyl- | —H | 2.78 |

TABLE 1-continued

| Cmpd | Structure | R₁ | R₂ | R₃ | R₄ | IC50 (μm) |
|---|---|---|---|---|---|---|
| 73 | 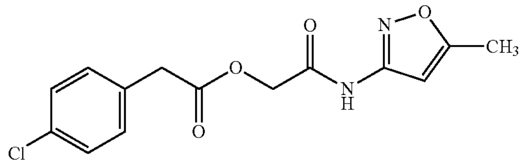 | 5-methyl-3-isoxazolyl- | —H | 4-chloro-phenyl- | —H | 2.9 |
| 74 | 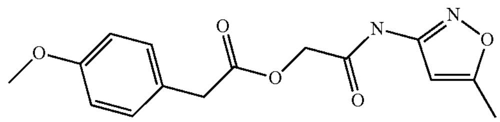 | 5-methyl-3-isoxazolyl- | —H | 4-methoxy-phenyl- | —H | 3.05 |
| 75 | 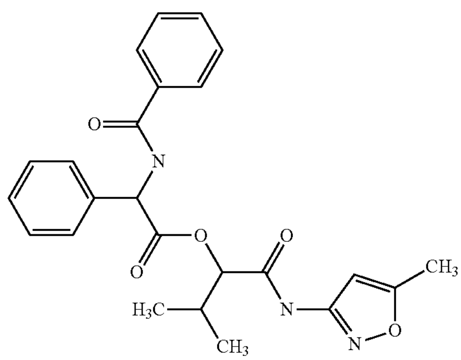 [SMILES: Cc1cc(NC(=O)C(OC(=O)C(NC(=O)c2ccccc2)c2ccccc2)C(C)C)no1] | 5-methyl-3-isoxazolyl- | -isopropyl | -benzamido | -phenyl | 3.26 |
| 76 | 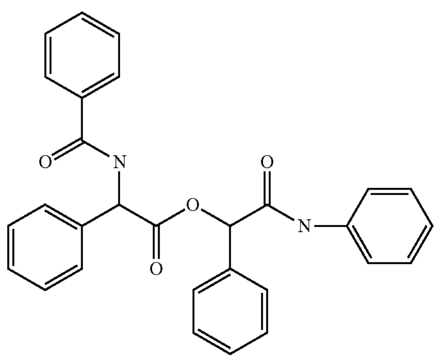 [SMILES: O=C(NC(C(=O)OC(C(=O)Nc1ccccc1)c1ccccc1)c1ccccc1)c1ccccc1] | -phenyl | -phenyl | -benzamido | -phenyl | 3.34 |
| 77 | 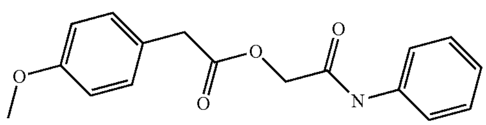 | -phenyl | —H | 4-methoxy-phenyl- | —H | 3.89 |
| 78 | 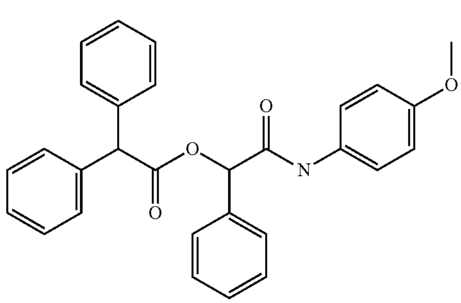 [SMILES: COc1ccc(NC(=O)C(OC(=O)C(c2ccccc2)c2ccccc2)c2ccccc2)cc1] | 4-methoxy-phenyl- | -phenyl | -phenyl | -phenyl | 4.33 |

TABLE 1-continued

| Cmpd | Structure | R₁ | R₂ | R₃ | R₄ | IC50 (μm) |
|---|---|---|---|---|---|---|
| 79 | 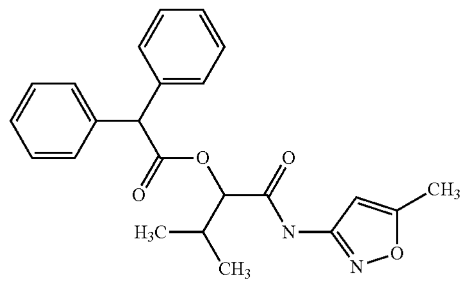 [SMILES: Cc1cc(NC(=O)C(OC(=O)C(c2ccccc2)c2ccccc2)C(C)C)no1] | 5-methyl-3-isoxazolyl- | -isopropyl | -phenyl | -phenyl | 4.56 |
| 80 | 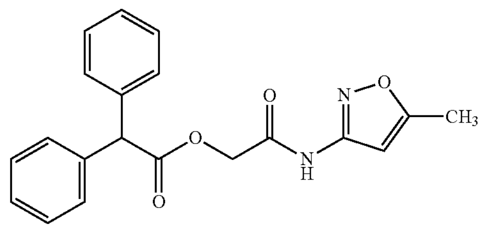 [SMILES: Cc1cc(NC(=O)COC(=O)C(c2ccccc2)c2ccccc2)no1] | 5-methyl-3-isoxazolyl- | —H | -phenyl | -phenyl | 4.70 |
| 81 | 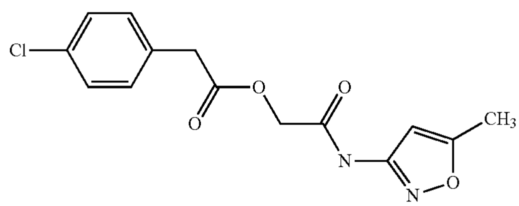 | 5-methyl-3-isoxazolyl- | —H | 4-chloro-phenyl- | —H | 5.0 |
| 82 | 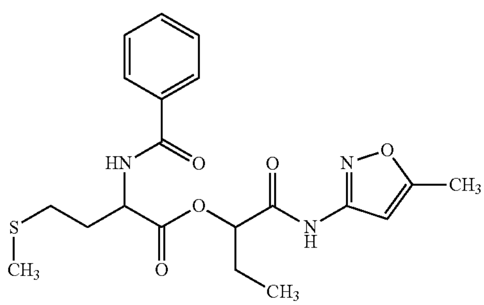 [SMILES: CCC(OC(=O)C(CCSC)NC(=O)c1ccccc1)C(=O)Nc1cc(C)on1] | 5-methyl-3-isoxazolyl- | —H | -benzamido | 2-methyl-sulfanyl ethyl- | 5.5 |
| 83 | 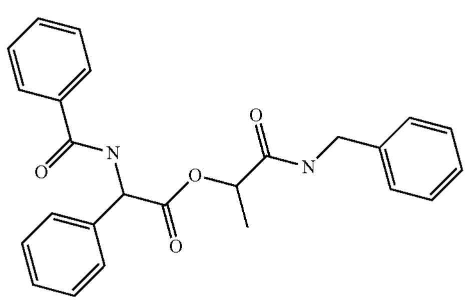 [SMILES: CC(OC(=O)C(NC(=O)c1ccccc1)c1ccccc1)C(=O)NCc1ccccc1] | -phenyl | -methyl | -benzamido | -phenyl | 5.89 |
| 84 | 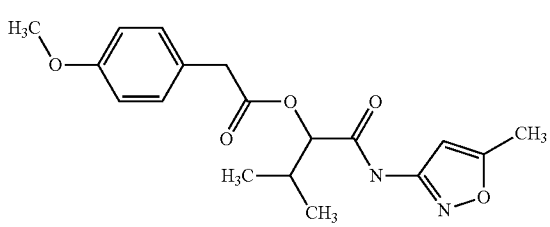 | 5-methyl-3-isoxazolyl- | -isopropyl | 4-methoxy-phenyl- | —H | 6.25 |

TABLE 1-continued
| Cmpd | Structure | $R_1$ | $R_2$ | $R_3$ | $R_4$ | IC50 (μm) |
|---|---|---|---|---|---|---|
| 85 | 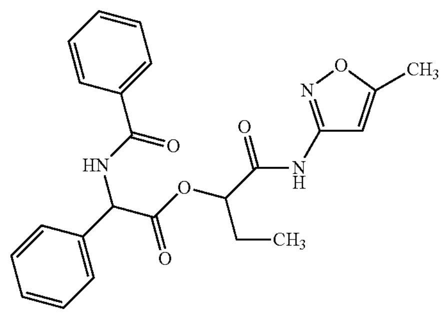 [SMILES: CCC(OC(=O)C(NC(=O)c1ccccc1)c1ccccc1)C(=O)Nc1cc(C)on1] | 5-methyl-3-isoxazolyl- | -ethyl | -benzamido | -phenyl | 6.43 |
| 86 | 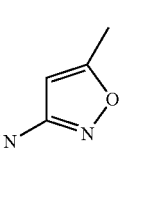 | 5-methyl-3-isoxazolyl- | —H | -phenyl | -phenyl | 6.64 |
| 87 | 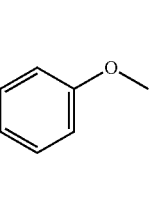 | 4-methoxy-phenyl- | —H | -phenyl | -phenyl | 7.39 |
| 88 | 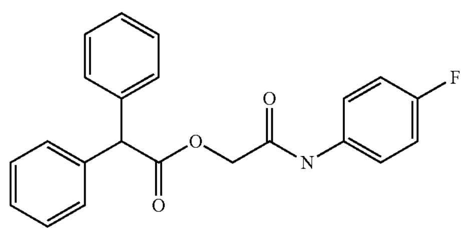 [SMILES: O=C(COC(=O)C(c1ccccc1)c1ccccc1)Nc1ccc(F)cc1] | 4-fluoro-phenyl- | —H | -phenyl | -phenyl | 8.49 |
| 89 | 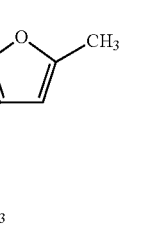 | 5-methyl-3-isoxazolyl- | -ethyl | -benzamido | -iso butanyl | 9.1 |
| 90 | 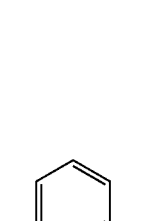 | -phenyl | —H | -phenyl | -phenyl | 11.2 |

TABLE 1-continued

| Cmpd | Structure | R₁ | R₂ | R₃ | R₄ | IC50 (μm) |
|---|---|---|---|---|---|---|
| 91 | 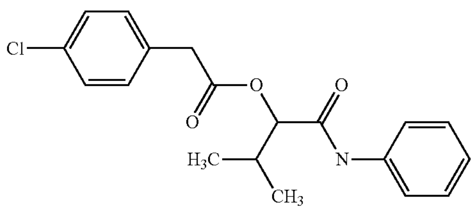 [SMILES: CC(C)C(OC(=O)Cc1ccc(Cl)cc1)C(=O)Nc1ccccc1] | -phenyl | -isopropyl | 4-chloro-phenyl- | —H | 4.1 |
| 92 | 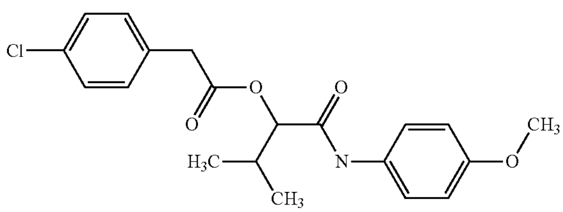 [SMILES: COc1ccc(NC(=O)C(OC(=O)Cc2ccc(Cl)cc2)C(C)C)cc1] | 4-methoxy-phenyl- | -isopropyl | 4-chloro-phenyl- | —H | 3.8 |
| 93 | 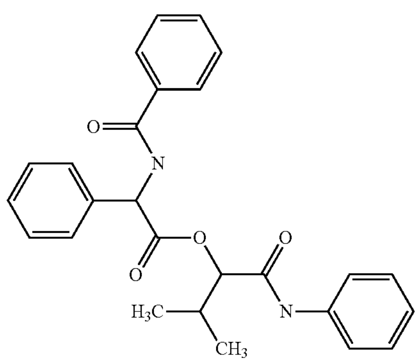 [SMILES: CC(C)C(OC(=O)C(NC(=O)c1ccccc1)c1ccccc1)C(=O)Nc1ccccc1] | -phenyl | -isopropyl | -benzamido | -phenyl | 2.3 |
| 94 | 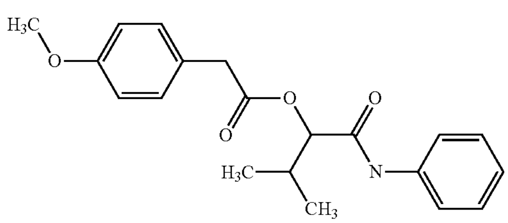 [SMILES: COc1ccc(CC(=O)OC(C(=O)Nc2ccccc2)C(C)C)cc1] | -phenyl | -isopropyl | 4-methoxy-phenyl- | —H | 3.6 |
| 95 | 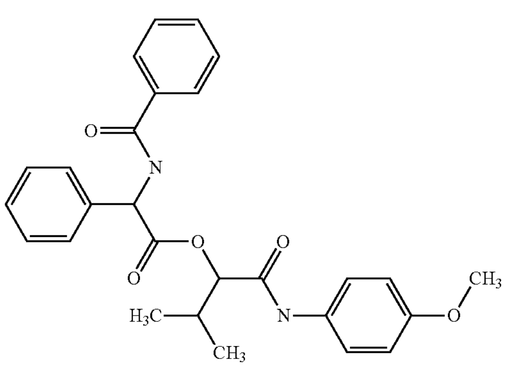 [SMILES: COc1ccc(NC(=O)C(OC(=O)C(NC(=O)c2ccccc2)c2ccccc2)C(C)C)cc1] | 4-methoxy-phenyl- | -isopropyl | -benzamido | -phenyl | 6.3 |

TABLE 1-continued

| Cmpd | Structure | R₁ | R₂ | R₃ | R₄ | IC50 (μm) |
|---|---|---|---|---|---|---|
| 96 | 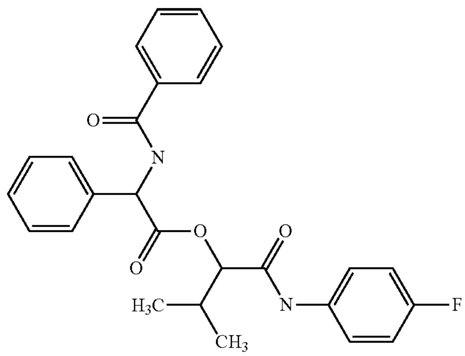 [SMILES: CC(C)C(OC(=O)C(NC(=O)c1ccccc1)c1ccccc1)C(=O)Nc1ccc(F)cc1] | 4-fluoro-phenyl- | -isopropyl | -benzamido | -phenyl | 3.7 |

General Synthesis Procedure

A round-bottomed flask was charged with the corresponding acid A (3.6 mmol), DIPEA (3.6 mmol) and DMF (1 mL). An appropriate 2-bromo- or 2-chloro-substituted acetamide B (3.0 mmol) was added under stirring. The resulting mixture was stirred at 100° C. for 2 h. Then it was cooled to ambient temperature and poured into solution of NaHCO₃ (2%, 7 mL). An oily product solidified after standing (2-5 h) at ambient temperature. A precipitate was filtered off, washed with solution of NaHCO₃ (2%, 2×7 mL), mixture of 2-propanol and water (1:1, 7 mL), water (7 mL) and dried. The crude material was re-crystallized from isopropanol.

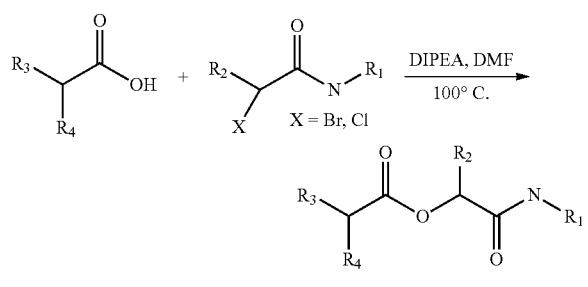

Example 1

[1-methyl-2-[(5-methylisoxazol-3-yl)amino]-2-oxo-ethyl] 2-(4-chlorophenyl)acetate ¹H-NMR (400 MHz, DMSO-d₆+CCl₄) δ ppm: 1.43 (3H, d, J=6.4 Hz, CH₃), 2.38 (3H, s, CH₃), 3.69 (2H, m, CH₂), 5.09 (1H, q, J=6.4 Hz, OCH), 6.60 (1H, s, isoxazole), 7.27 (4H, s, Ar), 10.89 (1H, br s, NH).

Example 3

1-[(5-methylisoxazol-3-yl)carbamoyl]propyl 2-(4-chlorophenyl)acetate

¹H-NMR (400 MHz, DMSO-d₆+CCl₄) δ ppm: 0.92 (3H, t, J=7.2 Hz, CH₃), 1.81 (2H, m, CH₂), 2.38 (3H, s, CH₃), 3.70 (2H, s, CH₂), 4.94 (1H, m, OCH), 6.61 (1H, s, isoxazole), 7.27 (4H, s, Ar), 10.93 (1H, br s, NH).

Example 4

[2-(4-methoxyanilino)-1-methyl-2-oxo-ethyl] 2-(4-chlorophenyl)acetate

¹H-NMR (400 MHz, DMSO-d₆) FIG. 1

Example 6

1-[(4-methoxyphenyl)carbamoyl]propyl 2-(4-chlorophenyl)acetate

¹H-NMR (400 MHz, DMSO-d₆) FIG. 2

Example 7

[1-methyl-2-[(5-methylisoxazol-3-yl)amino]-2-oxo-ethyl] 2-(4-methoxyphenyl) acetate ¹H-NMR (400 MHz, DMSO-d₆+CCl₄) δ ppm: 1.42 (3H, d, J=6.8 Hz, CH₃), 2.38 (3H, s, CH₃), 3.60 (2H, s, CH₂), 3.75 (3H, s, OCH₃), 5.05 (1H, q, J=6.8 Hz, OCH), 6.61 (1H, s, isoxazole), 6.79 (2H, d, J=8.4 Hz, Ar), 7.15 (2H, d, J=8.4 Hz, Ar), 10.93 (1H, br s, NH).

Example 8

1-[(4-fluorophenyl)carbamoyl]propyl 2-(4-chlorophenyl)acetate

¹H-NMR (400 MHz, DMSO-d₆) FIG. 3

Example 9

1-(phenylcarbamoyl)propyl 2-(4-chlorophenyl)acetate

¹H-NMR (500 MHz, DMSO) FIG. 4

Example 10

[2-(4-methoxyanilino)-1-methyl-2-oxo-ethyl] 3-cyclopentylpropanoate

¹H-NMR (400 MHz, DMSO-d₆) FIG. 5

Example 11

1-[(4-methoxyphenyl)carbamoyl]propyl 3-cyclopentylpropanoate

¹H-NMR (400 MHz, DMSO-d₆+CCl₄) FIG. 6

Example 13

[2-(4-methoxyanilino)-2-oxo-1-phenyl-ethyl] 2-(4-chlorophenyl)acetate

¹H-NMR (400 MHz, DMSO-d₆) FIG. 7

Example 14

[1-methyl-2-[(5-methylisoxazol-3-yl)amino]-2-oxo-ethyl] 3-cyclopentylpropanoate

¹H-NMR (400 MHz, DMSO-d₆) FIG. 8

Example 15

[2-(4-methoxyanilino)-1-methyl-2-oxo-ethyl] 2-(4-methoxyphenyl)acetate

¹H-NMR (400 MHz, DMSO-d₆) FIG. 9

Example 16

1-[(5-methylisoxazol-3-yl)carbamoyl]propyl 3-cyclopentylpropanoate

¹H-NMR (400 MHz, DMSO-d₆) FIG. 10

Example 19

[2-(4-methoxyanilino)-2-oxo-1-phenyl-ethyl] 3-cyclopentylpropanoate

¹H-NMR (400 MHz, DMSO-d₆) FIG. 11

Example 20

[2-[(5-methylisoxazol-3-yl)amino]-2-oxo-1-phenyl-ethyl] 3-cyclopentylpropanoate

¹H-NMR (400 MHz, DMSO-d₆) FIG. 12

Example 23

1-[(5-methylisoxazol-3-yl)carbamoyl]propyl 2-(4-methoxyphenyl)acetate

¹H-NMR (400 MHz, DMSO-d₆+CCl₄) FIG. 13

Example 24

1-[(4-methoxyphenyl)carbamoyl]propyl 2-(4-methoxyphenyl)acetate

¹H-NMR (500 MHz, DMSO) FIG. 14

Example 25

1-[(4-fluorophenyl)carbamoyl]propyl 3-cyclopentylpropanoate

¹H-NMR (400 MHz, DMSO-d₆) FIG. 15

Example 30

1-[(4-fluorophenyl)carbamoyl]propyl 2-(4-methoxyphenyl)acetate

¹H-NMR (400 MHz, DMSO-d₆) FIG. 16

Example 32

(2-anilino-2-oxo-1-phenyl-ethyl) 2-(4-chlorophenyl)acetate

¹H-NMR (400 MHz, DMSO-d₆) FIG. 17

Example 35

[2-(4-methoxyanilino)-2-oxo-1-phenyl-ethyl] 2-(4-methoxyphenyl)acetate

¹H-NMR (400 MHz, DMSO-d₆+CCl₄) δ ppm: 3.65-3.75 (5H, m, CH₂, OCH₃), 3.76 (3H, s, OCH₃), 5.98 (1H, s, OCH), 6.76 (2H, d, J=8.0 Hz, Ar), 6.81 (2H, d, J=8.0 Hz, Ar), 7.21 (2H, d, J=8.0 Hz, Ar), 7.26-7.38 (3H, m, Ar), 7.45 (2H, d, J=8.0 Hz, Ar), 7.53 (2H, d, J=6.8 Hz, Ar), 9.91 (1H, br s, NH).

Example 36

[2-[(5-methylisoxazol-3-yl)amino]-2-oxo-1-phenyl-ethyl] 2-(4-methoxyphenyl)acetate ¹H-NMR (400 MHz, DMSO-d₆) FIG. 18

Example 37

[2-(benzylamino)-2-oxo-1-phenyl-ethyl] 3-cyclopentylpropanoate

¹H-NMR (400 MHz, DMSO-d₆) FIG. 19

Example 42

[2-(4-methoxyanilino)-2-oxo-ethyl] 2-(4-chlorophenyl)acetate

¹H-NMR (400 MHz, DMSO-d₆+CCl₄) δ ppm: 1.44 (3H, d, J=6.8 Hz, CH₃), 3.63 (2H, m, CH₂), 3.75 (3H, s, OCH₃), 5.07 (1H, q, J=6.8 Hz, CH), 6.80 (2H, d, J=8.4 Hz, Ar), 6.96 (2H, m, Ar), 7.18 (2H, d, J=8.4 Hz, Ar), 7.58 (2H, m, Ar), 9.74 (1H, br s, NH).

Example 44

1-[(4-fluorophenyl)carbamoyl]propyl 2,2-diphenylacetate

¹H-NMR (500 MHz, DMSO-d₆+CCl₄) δ ppm: 0.87 (3H, t, J=7.5 Hz, CH₃), 1.82 (2H, m, CH₂), 4.97 (1H, m, OCH), 5.21 (1H, s, CH), 6.99 (2H, m, Ar), 7.18-7.38 (10H, m, Ar), 7.59 (2H, m, Ar), 9.87 (1H, br s, NH).

Example 47

[1-methyl-2-[(5-methylisoxazol-3-yl)amino]-2-oxo-ethyl] 2,2-diphenylacetate $^1$H-NMR (400 MHz, DMSO-d$_6$+CCl$_4$) δ ppm: 1.42 (3H, d, J=6.8 Hz, CH$_3$), 2.39 (3H, s, CH$_3$), 5.11 (1H, q, J=6.8 Hz, OCH), 5.16 (1H, s, CH), 6.64 (1H, s, isoxazole), 7.15-7.35 (10H, m, Ar), 11.01 (1H, s, NH).

Example 48

1-(phenylcarbamoyl)propyl 2,2-diphenylacetate $^1$H-NMR (400 MHz, DMSO-d$_6$) FIG. 20

Example 52

[1-methyl-2-[(5-methylisoxazol-3-yl)amino]-2-oxo-ethyl] 2-benzamido-2-phenyl-acetate $^1$H-NMR (500 MHz, DMSO) FIG. 21

Example 60

[2-[(5-methylisoxazol-3-yl)amino]-2-oxo-ethyl] 2-benzamido-2-phenyl-acetate $^1$H-NMR (500 MHz, CDCl$_3$) FIG. 22

Example 79

[2-methyl-1-[(5-methylisoxazol-3-yl)carbamoyl] propyl] 2,2-diphenylacetate $^1$H-NMR (500 MHz, DMSO-d$_6$+CCl$_4$) δ ppm: 0.75 (3H, d, J=6.5 Hz, CH$_3$), 0.78 (3H, d, J 6.5 Hz, CH$_3$), 2.09 (1H, m, CH), 2.35 (3H, s, CH$_3$), 4.83 (1H, d, J=5.0 Hz, OCH), 5.32 (1H, s, CH), 6.61 (1H, s, isoxazole), 7.20-7.39 (10H, m, Ar), 11.17 (1H, s, NH).

Example 94

[2-methyl-1-(phenylcarbamoyl)propyl] 2-(4-methoxyphenyl)acetate $^1$H-NMR (500 MHz, DMSO-d$_6$+CCl$_4$) δ ppm: 0.94 (6H, d, J=6.5 Hz, CH$_3$), 2.19 (1H, m, CH), 3.66 (2H, m, CH$_2$), 3.76 (3H, s, OCH$_3$), 4.80 (1H, d, J=5.5 Hz, OCH), 6.81 (2H, d, J=8.5 Hz, Ar), 6.99 (1H, t, J=7.3 Hz, Ar), 7.18-7.26 (4H, m, Ar), 7.56 (2H, d, J=8.0 Hz, Ar), 9.66 (1H, s, NH).

The invention claimed is:

1. A method for the prophylaxis, prevention, and/or treatment of a skin disease which comprising: administrating a therapeutically active amount of a compound according to Formula I or a pharmaceutical acceptable salt thereof to a subject in need of such treatment,

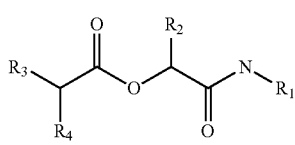

Formula I wherein $R_1$ is selected from aryl, substituted aryl, heteroaryl, and substituted heteroaryl;

$R_2$ is selected from hydrogen, alkyl, substituted alkyl, aryl, and substituted aryl;

$R_3$ is selected from alkyl, substituted alkyl, cycloalkyl, substituted cycloalkyl, aryl, substituted aryl, heteroaryl, substituted heteroaryl, and —C$_1$-C$_3$-alkyl-R$_5$, wherein $R_5$ is selected from cycloalkyl, substituted cycloalkyl, aryl, substituted aryl, heteroaryl, substituted heteroaryl;

$R_4$ is selected from hydrogen, alkyl, substituted alkyl, aryl, substituted aryl, heteroaryl, and substituted heteroaryl, and —NH—CO—R$_6$, wherein $R_6$ is selected from aryl and substituted aryl, heteroaryl, and substituted heteroaryl.

2. A compound selected from the group consisting of
[1-methyl-2-[(5-methylisoxazol-3-yl)amino]-2-oxo-ethyl]2-(4-chlorophenyl)acetate,
1-[(5-methylisoxazol-3-yl)carbamoyl]propyl 2-(4-chlorophenyl)acetate,
[1-methyl-2-[(5-methylisoxazol-3-yl)amino]-2-oxo-ethyl]2-(4-methoxyphenyl)acetate,
1-[(5-methylisoxazol-3-yl)carbamoyl]propyl 2-(4-methoxyphenyl)acetate,
[1-methyl-2-[(5-methylisoxazol-3-yl)amino]-2-oxo-ethyl]3-cyclopentylpropanoate,
[2-(4-methoxyanilino)-1-methyl-2-oxo-ethyl]2-(4-methoxyphenyl)acetate,
1-[(5-methylisoxazol-3-yl)carbamoyl]propyl 3-cyclopentylpropanoate,
[2-[(5-methylisoxazol-3-yl)amino]-2-oxo-1-phenyl-ethyl]2-(4-chlorophenyl)acetate,
[2-[(5-methylisoxazol-3-yl)amino]-2-oxo-1-phenyl-ethyl]3-cyclopentylpropanoate,
1-[(5-methylisoxazol-3-yl)carbamoyl]propyl 2-(4-methoxyphenyl)acetate,
1-[(5-methylisoxazol-3-yl)carbamoyl]propyl 2-(1,3-benzodioxol-5-yl)acetate,
[2[(5-methylisoxazol-3-yl)amino]-2-oxo-1-phenyl-ethyl] 2-(4-methoxyphenyl)acetate,
1-[(5-methylisoxazol-3-yl)carbamoyl]propyl 2-(3,4-dichlorophenyl)acetate,
1-[(5-methylisoxazol-3-yl)carbamoyl]propyl 2-(3,4-dimethoxyphenyl)acetate,
[1-methyl-2-[(5-methylisoxazol-3-yl)amino]-2-oxo-ethyl]2,2-diphenylacetate,
[2[(5-methylisoxazol-3-yl)amino]-2-oxo-1-phenyl-ethyl] 2-benzamido-2-phenyl-acetate,
[1-methyl-2-[(5-methylisoxazol-3-yl)amino]-2-oxo-ethyl]2-benzamido-2-phenyl-acetate,
[2-[(5-methylisoxazol-3-yl)amino]-2-oxo-1-phenyl-ethyl]2,2-diphenylacetate,
[2[(5-methylisoxazol-3-yl)amino]-2-oxo-ethyl]2-benzamido-2-phenyl-acetate,
[2-methyl-1-[(5-methylisoxazol-3-yl)carbamoyl]propyl] 2-(4-chlorophenyl)acetate,
[2-methyl-1-[(5-methylisoxazol-3-yl)carbamoyl]propyl] 3-cyclopentylpropanoate,
[2-methyl-1-[(5-methylisoxazol-3-yl)carbamoyl]propyl] 2-benzamido-2-phenyl-acetate,
[2-methyl-1-[(5-methylisoxazol-3-yl)carbamoyl]propyl] 2,2-diphenylacetate,
[2-[(5-methylisoxazol-3-yl)amino]-2-oxo-ethyl]2-(4-chlorophenyl)acetate, and
[2-methyl-1-[(5-methylisoxazol-3-yl)carbamoyl]propyl] 2-(4-methoxyphenyl)acetate.

3. A compound selected from the group consisting of
[2-(4-methoxyanilino)-1-methyl-2-oxo-ethyl]2-(4-chlorophenyl)acetate,
1-[(4-methoxyphenyl)carbamoyl]propyl 2-(4-chlorophenyl)acetate,
1-[(4-fluorophenyl)carbamoyl]propyl 2-(4-chlorophenyl)acetate,
1-(phenylcarbamoyl)propyl 2-(4-chlorophenyl)acetate,
[2-(4-methoxyanilino)-1-methyl-2-oxo-ethyl]3-cyclopentylpropanoate,
1-[(4-methoxyphenyl)carbamoyl]propyl 3-cyclopentylpropanoate,
[2-(4-methoxyanilino)-2-oxo-1-phenyl-ethyl]2-(4-chlorophenyl)acetate,
[2-(4-methoxyanilino)-2-oxo-1-phenyl-ethyl]3-cyclopentylpropanoate,
1-[(4-methoxyphenyl)carbamoyl]propyl 2-(4-methoxyphenyl)acetate,
1-[(4-fluorophenyl)carbamoyl]propyl 3-cyclopentylpropanoate,
1-[(4-fluorophenyl)carbamoyl]propyl 2-(4-methoxyphenyl)acetate,
(2-anilino-1-methyl-2-oxo-ethyl) 3-cyclopentylpropanoate,
(2-anilino-2-oxo-1-phenyl-ethyl) 2-(4-chlorophenyl)acetate,
1-(phenylcarbamoyl)propyl 2-(4-methoxyphenyl)acetate,
[2-(4-methoxyanilino)-2-oxo-1-phenyl-ethyl]2-(4-methoxyphenyl)acetate,
[2-(benzylamino)-2-oxo-1-phenyl-ethyl]3-cyclopentylpropanoate,
[2-(4-methoxyanilino)-2-oxo-ethyl]2-(4-methoxyphenyl)acetate,
1-[(4-methoxyphenyl)carbamoyl]propyl 2,2-diphenylacetate,
1-[(4-fluorophenyl)carbamoyl]propyl 2,2-diphenylacetate,
1-(phenylcarbamoyl)propyl 2,2-diphenylacetate,
[2-(4-methoxyanilino)-2-oxo-ethyl]2-benzamido-2-phenyl-acetate,
[2-(4-fluoroanilino)-2-oxo-ethyl]2-benzamido-2-phenyl-acetate,
(2-anilino-2-oxo-ethyl) 2-benzamido-2-phenyl-acetate,
1-[(4-methoxyphenyl)carbamoyl]propyl 2-benzamido-2-phenyl-acetate,
1-[(4-fluorophenyl)carbamoyl]propyl 2-benzamido-2-phenyl-acetate,
(2-anilino-1-methyl-2-oxo-ethyl) 2-benzamido-2-phenyl-acetate,
[2-(4-methoxyanilino)-1-methyl-2-oxo-ethyl]2-benzamido-2-phenyl-acetate,
(2-anilino-2-oxo-1-phenyl-ethyl) 2-benzamido-2-phenyl-acetate,
[2-(4-methoxyanilino)-2-oxo-1-phenyl-ethyl]2,2-diphenylacetate,
[2-(benzylamino)-1-methyl-2-oxo-ethyl]2-benzamido-2-phenyl-acetate,
[2-methyl-1-(phenylcarbamoyl)propyl]2-(4-chlorophenyl)acetate,
[1-[(4-methoxyphenyl)carbamoyl]-2-methyl-propyl]2-(4-chlorophenyl)acetate,
[2-methyl-1-(phenylcarbamoyl)propyl]2-benzamido-2-phenyl-acetate,
[2-methyl-1-(phenylcarbamoyl)propyl]2-(4-methoxyphenyl)acetate,
[1-[(4-methoxyphenyl)carbamoyl]-2-methyl-propyl]2-benzamido-2-phenyl-acetate, and
[1-[(4-fluorophenyl)carbamoyl]-2-methyl-propyl]2-benzamido-2-phenyl-acetate.

4. A pharmaceutical composition comprising a compound according to claim 2 in admixture with at least one of pharmaceutically acceptable adjuvants, diluents, and carriers.

5. The compound according to claim 2 for use in medicine.

6. The compound according to claim 2 for use in prophylaxis, prevention, and treatment of skin diseases.

7. The according to claim 6, wherein the skin disease is an inflammatory skin disease.

8. The compound according to claim 6, wherein the skin disease is selected from Netherton syndrome, atopic dermatitis, contact dermatitis, eczema, psoriasis, acne, epidermal hyperkeratosis, acanthosis, epidermal inflammation, dermal inflammation and pruritus.

9. A cosmetic or skin care composition comprising at least one compound according to claim 2, or a pharmaceutically acceptable salt thereof, said composition being in a form suitable for topical administration, and selected from the group consisting of a cream, an ointment, a lotion, a liniment, a gel, a paste, a stick, a spray, a shampoo, a soap, a hair conditioner and a powder.

10. A pharmaceutical composition comprising a compound according to claim 3 in admixture with at least one of pharmaceutically acceptable adjuvants, diluents, and carriers.

11. The compound according to claim 3 for use in medicine.

12. The compound according to claim 3 for use in prophylaxis, prevention, and treatment of skin diseases.

13. The compound according to claim 12, wherein the skin disease is an inflammatory skin disease.

14. The compound according to claim 12, wherein the skin disease is selected from Netherton syndrome, atopic dermatitis, contact dermatitis, eczema, psoriasis, acne, epidermal hyperkeratosis, acanthosis, epidermal inflammation, dermal inflammation and pruritus.

15. A cosmetic or skin care composition comprising at least one compound according to claim 3, or a pharmaceutically acceptable salt thereof, said composition being in a form suitable for topical administration, and selected from the group consisting of a cream, an ointment, a lotion, a liniment, a gel, a paste, a stick, a spray, a shampoo, a soap, a hair conditioner and a powder.

* * * * *

UNITED STATES PATENT AND TRADEMARK OFFICE
CERTIFICATE OF CORRECTION

PATENT NO. : 9,744,148 B2  
APPLICATION NO. : 15/113658  
DATED : August 29, 2017  
INVENTOR(S) : Marcel Linschoten Page 1 of 1

It is certified that error appears in the above-identified patent and that said Letters Patent is hereby corrected as shown below:

On the Title Page

Item (30) At Column 1, Line number 30, under Foreign Application Priority Date, Jan. 23, 2014 (SE) should read 1430004-0.

Signed and Sealed this
Twelfth Day of November, 2019

Andrei Iancu
*Director of the United States Patent and Trademark Office*